United States Patent
Harada

(10) Patent No.: US 11,653,823 B2
(45) Date of Patent: May 23, 2023

(54) ENDOSCOPE

(71) Applicant: FUJIFILM Corporation, Tokyo (JP)

(72) Inventor: Takashi Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 238 days.

(21) Appl. No.: 16/905,867

(22) Filed: Jun. 18, 2020

(65) Prior Publication Data

US 2020/0315428 A1 Oct. 8, 2020

Related U.S. Application Data

(63) Continuation of application No. PCT/JP2018/047059, filed on Dec. 20, 2018.

(30) Foreign Application Priority Data

Jan. 29, 2018 (JP) .............................. JP2018-012781

(51) Int. Cl.
*A61B 1/005* (2006.01)
*A61B 1/00* (2006.01)
(Continued)

(52) U.S. Cl.
CPC ........ *A61B 1/0057* (2013.01); *A61B 1/00006* (2013.01); *A61B 1/00066* (2013.01);
(Continued)

(58) Field of Classification Search
CPC . A61B 1/0057; A61B 1/0006; A61B 1/00066; A61B 1/00087; A61B 1/00112;
(Continued)

(56) References Cited

U.S. PATENT DOCUMENTS 5,569,157 A * 10/1996 Nakazawa ............. A61B 1/018
600/106
2019/0246886 A1 8/2019 Harada et al.

FOREIGN PATENT DOCUMENTS

JP H06315458 11/1994
JP H1099266 4/1998
(Continued)

OTHER PUBLICATIONS

"International Search Report (Form PCT/ISA/210) of PCT/JP2018/047059" dated Mar. 5, 2019, with English translation thereof, pp. 1-3.
(Continued)

*Primary Examiner* — Ryan N Henderson
*Assistant Examiner* — Megan Elizabeth Monahan
(74) *Attorney, Agent, or Firm* — JCIPRNET

(57) ABSTRACT

There is provided an endoscope that allows the distal end portion of a wire and a treatment tool-elevator to be easily connected to each other. An engaging portion (100) is provided at the distal end portion of a wire (60). An elevator (30) is provided with a contact portion (101) that applies a rotational moving force acting in a fallen direction to the elevator (30) in a case where the engaging portion (100) is in contact with the contact portion. The elevator (30) is provided with a housing portion (102) in which an opening (104) is formed. A wall portion (81) is provided at a position that faces the movement trajectory of the engaging portion (100) in a case where the elevator (30) is moved between an elevated position and a fallen position in a state where the engaging portion (100) is in contact with the contact portion (101). In a state where the engaging portion (100) is in contact with the contact portion (101), the wall portion (81) regulates the movement of the engaging portion (100) in a direction where the engaging portion (100) enters the opening (104) in a case where the elevator (30) is present
(Continued)

between the elevated position and the fallen position and allows the movement of the engaging portion (100) in the direction where the engaging portion (100) enters the opening (104) in a case where the elevator (30) is present between the fallen position and an attachment/detachment position.

12 Claims, 34 Drawing Sheets

(51) Int. Cl.
     *A61B 1/01*      (2006.01)
     *A61B 1/018*     (2006.01)

(52) U.S. Cl.
     CPC ...... *A61B 1/00087* (2013.01); *A61B 1/00112* (2013.01); *A61B 1/00137* (2013.01); *A61B 1/01* (2013.01); *A61B 1/018* (2013.01)

(58) Field of Classification Search
     CPC ....... A61B 1/00137; A61B 1/01; A61B 1/018; A61B 1/00098; A61B 1/0676; A61B 1/00101; A61B 1/00128
     See application file for complete search history.

(56) References Cited

FOREIGN PATENT DOCUMENTS

| | | |
|---|---|---|
| JP | H11299728 | 11/1999 |
| WO | 2018100823 | 6/2018 |

OTHER PUBLICATIONS

"Written Opinion of the International Searching Authority (Form PCT/ISA/237) of PCT/JP2018/047059," dated Mar. 5, 2019, with English translation thereof, pp. 1-9.

\* cited by examiner

FIG. 3
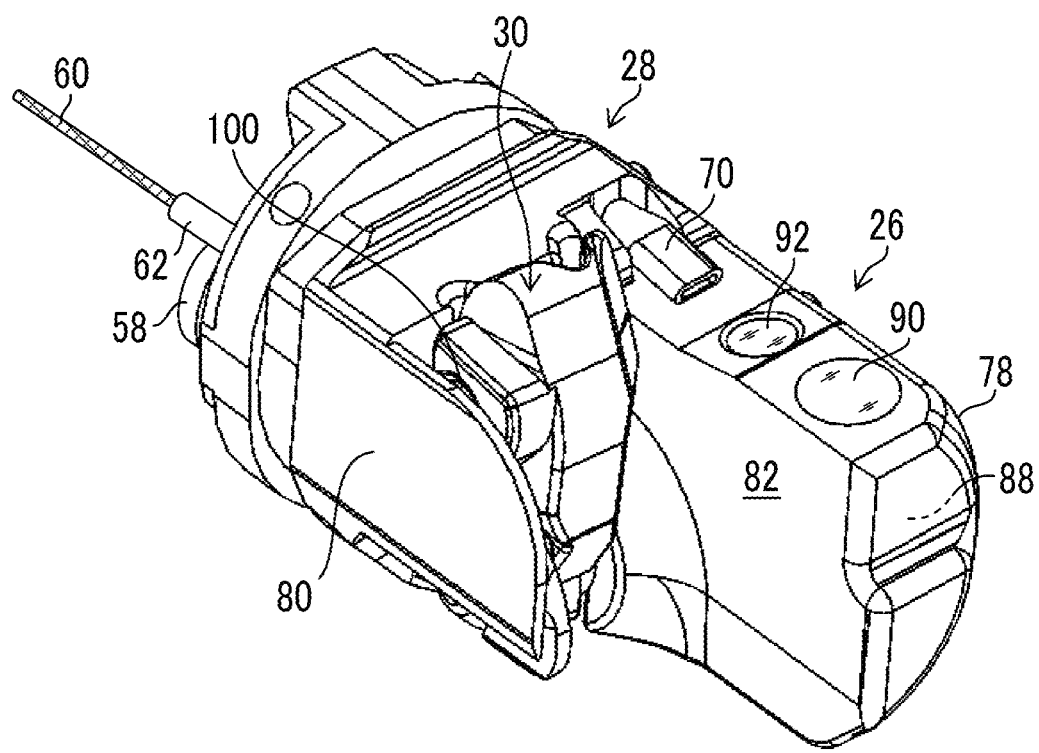
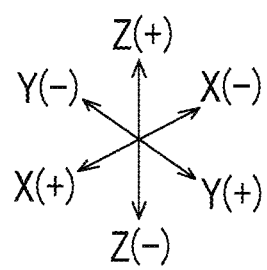

FIG. 4
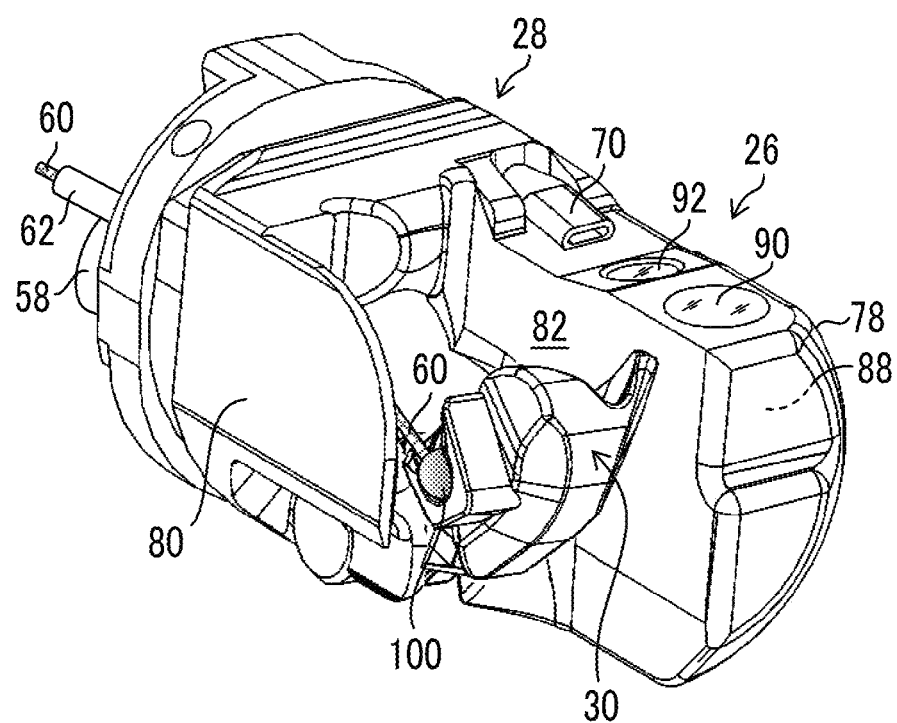
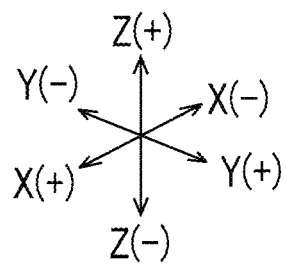

FIG. 5
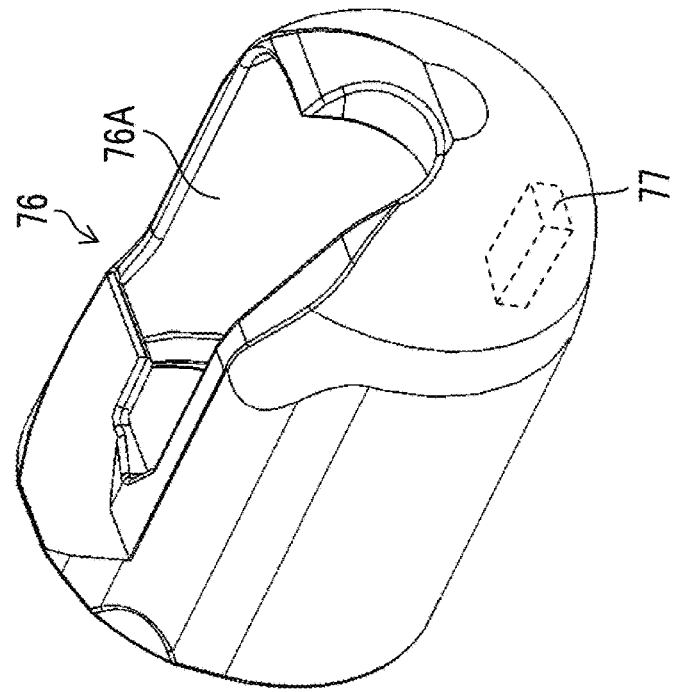
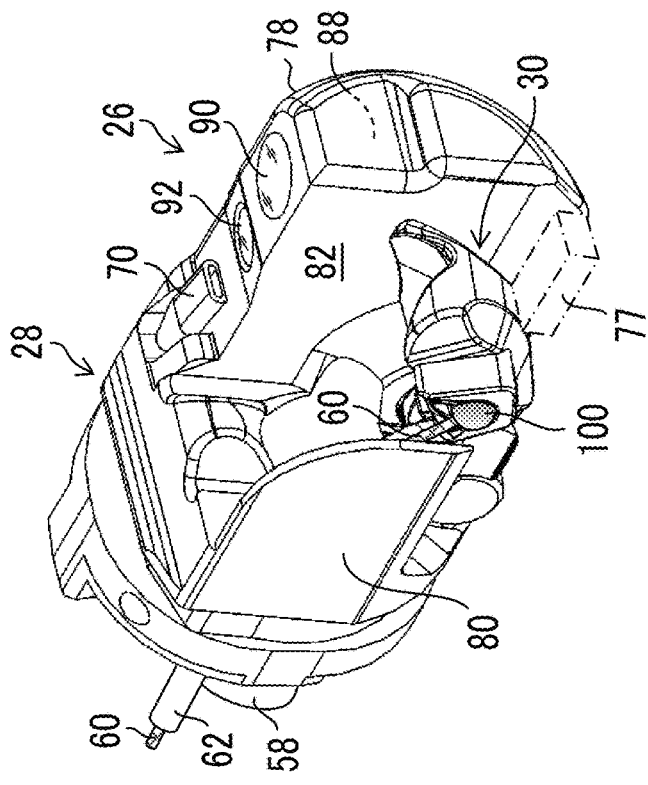
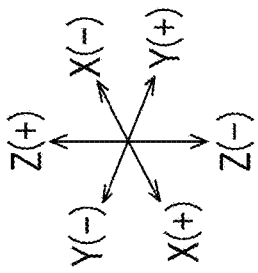

FIG. 7
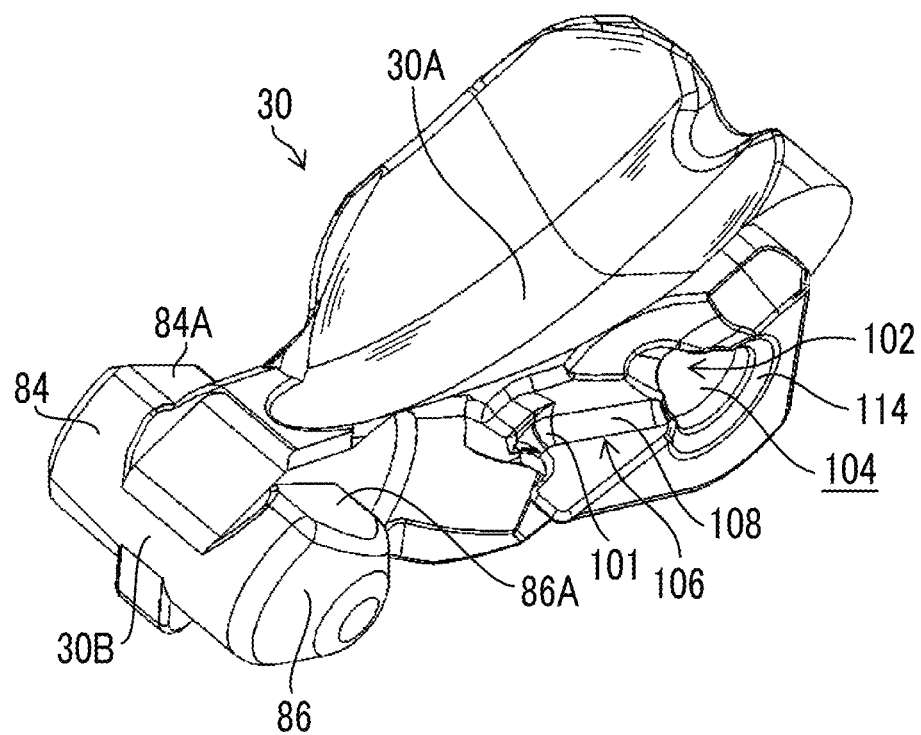
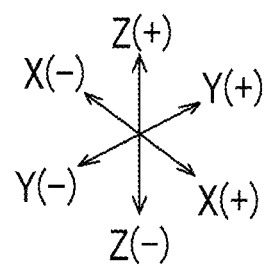

FIG. 10
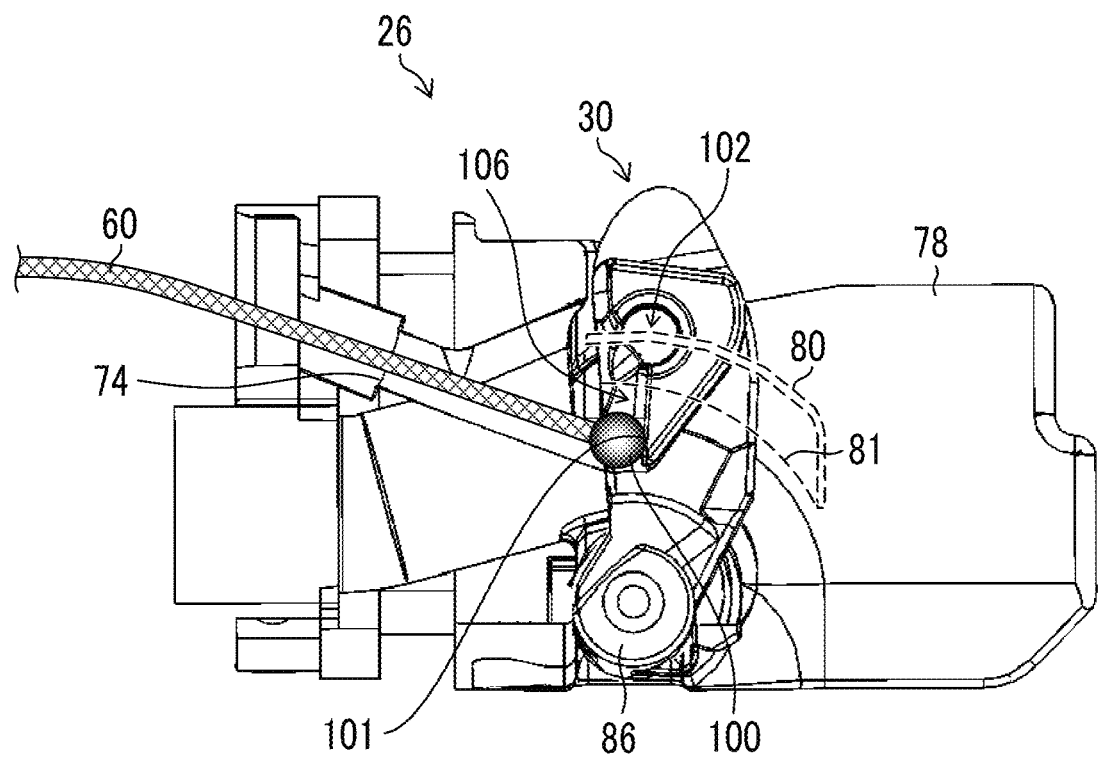
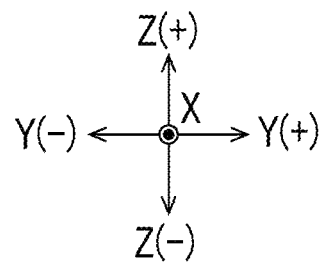

FIG. 15
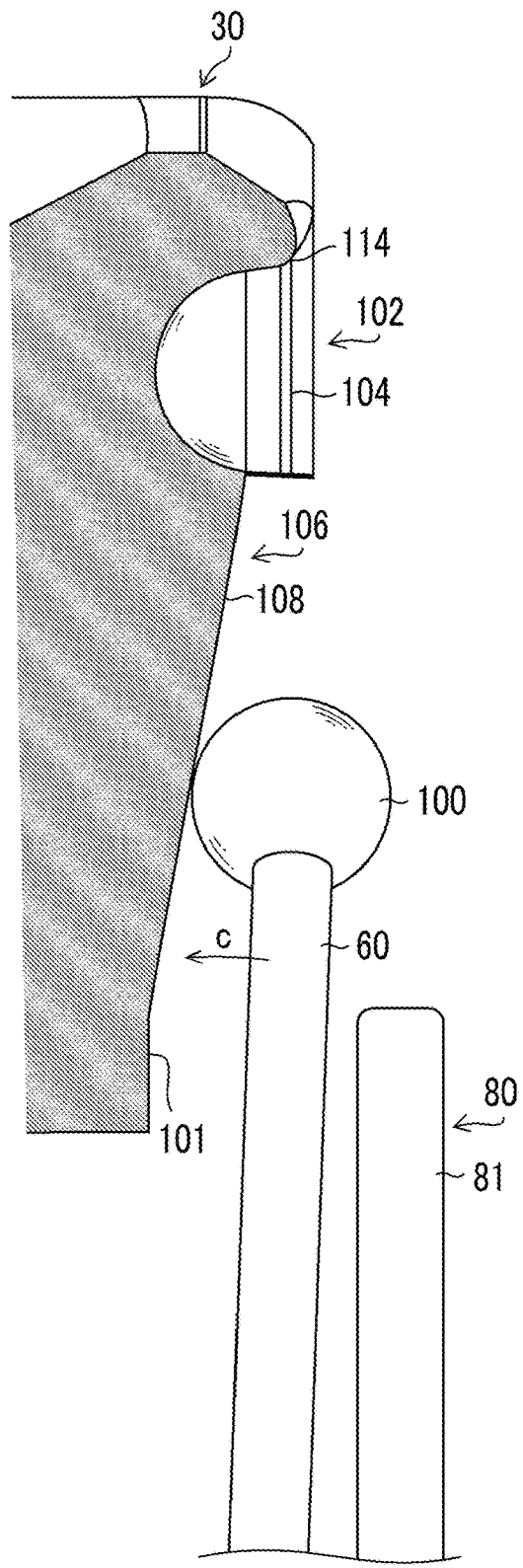
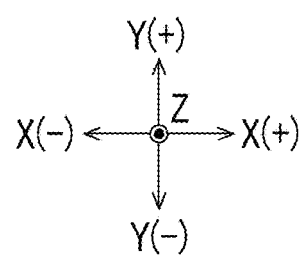

FIG. 23
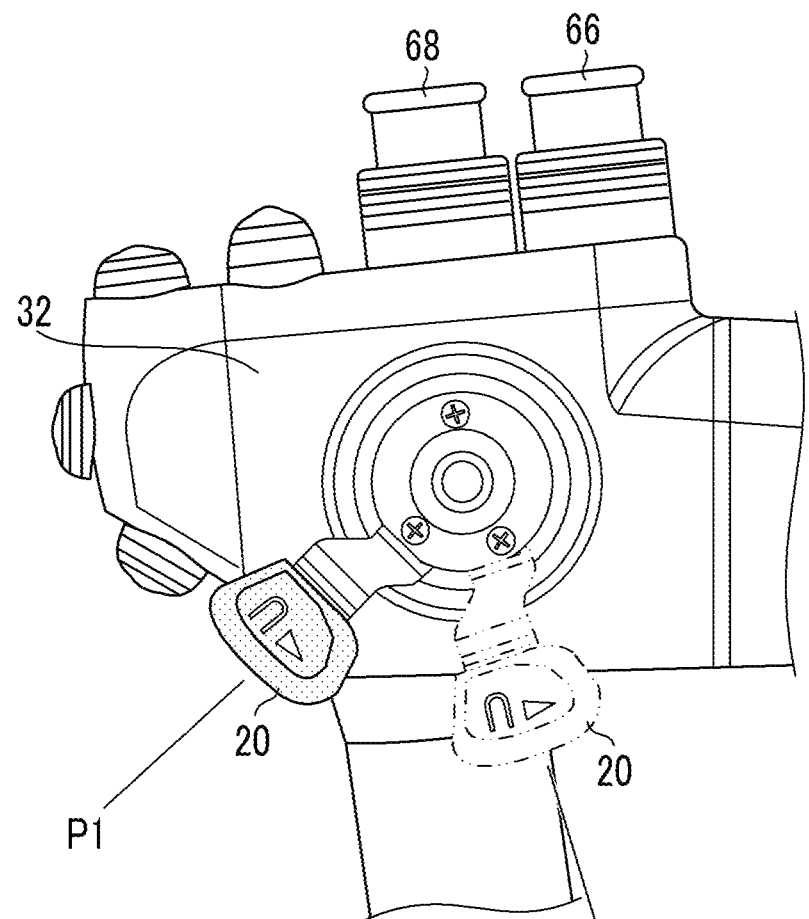
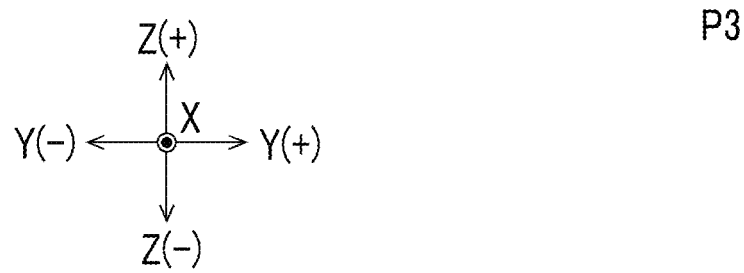

FIG. 32
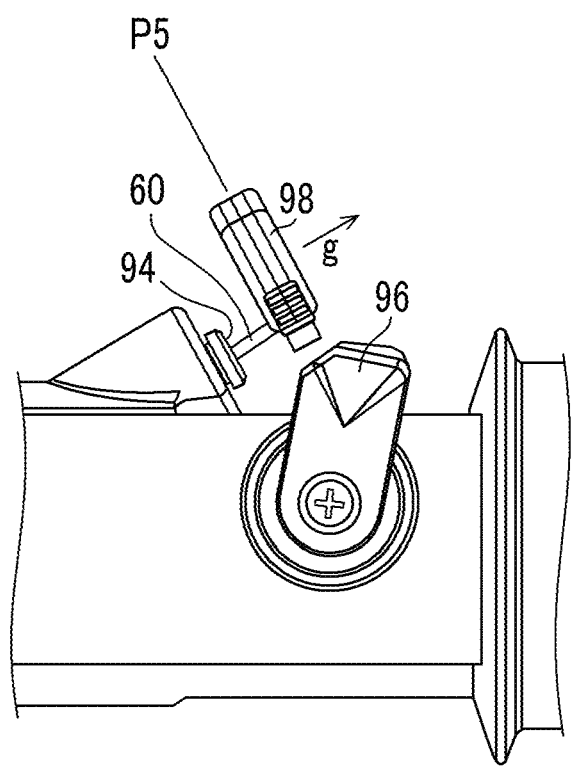
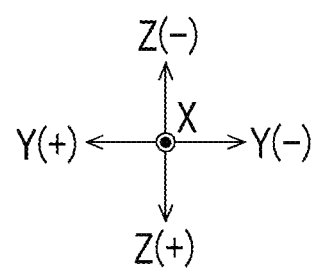

ENDOSCOPE

CROSS-REFERENCE TO RELATED APPLICATIONS

The present application is a Continuation of PCT International Application No. PCT/JP2018/047059 filed on Dec. 20, 2018 claiming priority under 35 U.S.C. § 119(a) to Japanese Patent Application No. 2018-012781 filed on Jan. 29, 2018. Each of the above applications is hereby expressly incorporated by reference, in its entirety, into the present application.

BACKGROUND OF THE INVENTION

1. Field of the Invention

The present invention relates to an endoscope, and more particularly, to an endoscope of which a distal end part of an insertion unit comprises a treatment tool-elevator for changing the lead-out direction of a treatment tool.

2. Description of the Related Art

In an endoscope, various treatment tools are introduced through a treatment tool inlet provided on a hand operation unit (hereinafter referred to as an "operation unit"), are led out of a treatment tool outlet opened to a distal end member of the insertion unit to the outside, and are used for treatment. For example, a treatment tool, such as forceps or a contrast tube, is used in a duodenoscope, and a treatment tool, such as a puncture needle, is used in an ultrasound endoscope. The lead-out direction of such a treatment tool needs to be changed at the distal end member to perform treatment at a desired position in an object to be examined. For this purpose, the distal end member is provided with a treatment tool-elevator (also referred to as a forceps-elevator. Hereinafter referred to as an "elevator"), and the operation unit is provided with a treatment tool-elevating mechanism that changes the attitude of the elevator between an elevated position and a fallen position.

A wire pulling mechanism where the distal end portion of a wire (also referred to as an elevating wire) is directly mounted on an elevator is known as the treatment tool-elevating mechanism (see JP1994-315458A (JP-H06-315458A)). In this mechanism, the proximal end side of a wire is connected to an elevating operation lever (also referred to as an elevating lever) provided on an operation unit and the elevator is rotated about a rotational movement shaft to change the attitude thereof between an elevated position and a fallen position in a case where the wire is pushed or pulled by the elevating operation lever.

Incidentally, in a case where an endoscope is used for various examinations or treatments, body cavity liquid adheres to the distal end member of the insertion unit comprising the elevator and a guide pipe into which the wire is to be inserted. For this reason, after being used, the endoscope is washed and disinfected using a washing solution and an antiseptic solution. In this case, since the diameter of the guide pipe is small and the wire is inserted into the guide pipe, time and effort are required for washing.

Accordingly, a cover for covering a distal end member of an insertion unit, an elevator, and a wire are attachably and detachably provided in an endoscope disclosed in JP1994-315458A (JP-H06-315458A); and the guide pipe for a wire is washed after the cover, the elevator, and the wire are detached.

Further, one example of an endoscope, which is adapted so that a wire can be attached to and detached from an elevator, is disclosed in JP1994-315458A (JP-H06-315458A). According to this endoscope, a tip is provided at the distal end portion of the wire and the elevator is provided with a tip housing portion that houses the tip.

According to the endoscope disclosed in JP1994-315458A (JP-H06-315458A), the tip of the used wire is detached from the tip housing portion of the elevator first and the used wire is then removed from the guide pipe. Next, the endoscope is washed. After that, a new wire is inserted into the guide pipe and a tip provided at the distal end portion of the wire is housed in the tip housing portion of the elevator, so that the distal end portion of the wire and the elevator are manually connected to each other.

SUMMARY OF THE INVENTION

However, since the distal end member of the insertion unit of the endoscope is reduced in size as the insertion unit is reduced in diameter, the tip of the wire disclosed in JP1994-315458A (JP-H06-315458A) also has a small size. There is a problem that much time and effort are required to manually house such a small tip in the tip housing portion of the elevator.

Since the endoscope disclosed in JP1994-315458A (JP-H06-315458A) is adapted so that only the used wire can be replaced with a new wire, an economical effect can be obtained but there is a problem that much time and effort are required to connect the distal end portion of a new wire to the elevator.

The invention has been made in consideration of the above-mentioned circumstances, and an object of the invention is to provide an endoscope that allows the distal end portion of a wire and a treatment tool-elevator to be easily connected to each other.

In order to achieve the object of the invention, an endoscope according to an aspect of the invention comprises a hand operation unit that comprises an operation member, an insertion unit of which a proximal end portion is connected to the hand operation unit, a distal end member that is provided at a distal end part of the insertion unit, a treatment tool-elevator that is mounted on the distal end member so as to be rotationally movable and is rotationally movable in a rotational movement range from an elevated position up to an attachment/detachment position beyond a fallen position, an elevating operation wire of which a distal end side is connected to the treatment tool-elevator and a proximal end side is connected to the operation member and which is pushed or pulled according to an operation of the operation member to cause the treatment tool-elevator to be rotationally moved in the rotational movement range between the elevated position and the fallen position, an engaging portion that is provided at a distal end portion of the elevating operation wire, an inlet which is provided on the hand operation unit and through which the elevating operation wire is introduced so that the engaging portion becomes a leading end, an outlet which is provided at the distal end member and out of which the elevating operation wire is led so that the engaging portion becomes a leading end, a wire insertion channel that is provided in the insertion unit and allows the inlet and the outlet to communicate with each other, a contact portion that is provided on the treatment tool-elevator and applies a rotational moving force acting in a fallen direction to the treatment tool-elevator in a case where the engaging portion led out of the outlet is in contact with the contact portion, a housing portion which is provided on the treatment tool-elevator and in which an opening for housing the engaging portion is formed, and a wall portion that is provided at a position adjacent to the treatment tool-elevator and facing a movement trajectory of the engaging portion in a case where the treatment tool-elevator is moved between the elevated position and the fallen position in a state where the engaging portion is in contact with the contact portion. In a state where the engaging portion is in contact with the contact portion, the wall portion regulates movement of the engaging portion in a direction where the engaging portion enters the opening in a case where the treatment tool-elevator is present between the elevated position and the fallen position and allows movement of the engaging portion in the direction where the engaging portion enters the opening in a case where the treatment tool-elevator is present between the fallen position and the attachment/detachment position.

In the aspect of the invention, it is preferable that the distal end member is provided with a wire guide portion that guides the engaging portion led out of the outlet to the contact portion.

In the aspect of the invention, it is preferable that the treatment tool-elevator is provided with a guide portion for engagement that guides the engaging portion to the opening.

In the aspect of the invention, it is preferable that the guide portion for engagement includes a guide passage that guides the engaging portion in a direction where the engaging portion is separated from the opening.

It is preferable that the endoscope according to the aspect of the invention further comprises a retaining portion that is provided at a position adjacent to the treatment tool-elevator and facing a movement trajectory of the engaging portion in a case where the treatment tool-elevator is moved between the elevated position and the fallen position in a state where the engaging portion is housed in the housing portion, and maintains a state where the housing portion and the engaging portion are engaged with each other.

In the aspect of the invention, it is preferable that a cap member is attachably and detachably mounted on the distal end member and any one of the distal end member or the cap member comprises the wall portion or the retaining portion.

In the aspect of the invention, it is preferable that the cap member comprises a position regulating member, and it is preferable that, in a case where the cap member is mounted on the distal end member, the position regulating member is in contact with the treatment tool-elevator and regulates a position where the treatment tool-elevator is most fallen to the attachment/detachment position.

In the aspect of the invention, it is preferable that an inclined surface for disengagement, which is widened toward an outside of the opening, is formed on an inner surface, which corresponds to a lead-out direction of the engaging portion, in an inner surface of the housing portion close to the opening.

It is preferable that the endoscope according to the aspect of the invention further comprises a movable member that is disposed to be exposed to an outside of the hand operation unit and operates in conjunction with an operation of the operation member and a mounting member that is provided at a proximal end of the elevating operation wire and is attachably and detachably engaged with the movable member.

In the aspect of the invention, it is preferable that any one of the movable member or the mounting member is provided with an engaging hole and the other thereof is provided with a locking portion to be attachably and detachably engaged with the engaging hole.

In the aspect of the invention, it is preferable that the locking portion is provided with an elastically deformable portion that is elastically deformed to be engaged with the engaging hole.

In the aspect of the invention, it is preferable that a pair of elastically deformable claw portions to be locked to edge portions of the engaging hole is formed at the elastically deformable portion and the pair of claw portions is displaced so as to approach each other through elastic deformation in a case where the engaging hole and the locking portion are engaged with each other or disengaged from each other.

According to the invention, the distal end portion of a wire and a treatment tool-elevator can be easily connected to each other.

BRIEF DESCRIPTION OF THE DRAWINGS

FIG. 3 is a perspective view of the distal end part of which an elevator is positioned at an elevated position.

FIG. 4 is a perspective view of the distal end part of which the elevator is positioned at a fallen position.

FIG. 5 is a perspective view of the distal end part of which the elevator is positioned at an attachment/detachment position.

FIG. 7 is an enlarged perspective view of the elevator.

FIG. 10 is a diagram illustrating a state where an engaging portion is in contact with a contact portion of the elevator positioned at the elevated position.

FIG. 15 is a diagram illustrating that the engaging portion is moved along a guide passage.

FIG. 23 is a diagram illustrating the operating range of an elevating operation lever.

FIG. 32 is a diagram illustrating the mounting member in a state where the distal end portion of the wire is connected to the elevator.

DESCRIPTION OF THE PREFERRED EMBODIMENTS

An endoscope according to a preferred embodiment of the invention will be described below with reference to the accompanying drawings.

Figure 1:
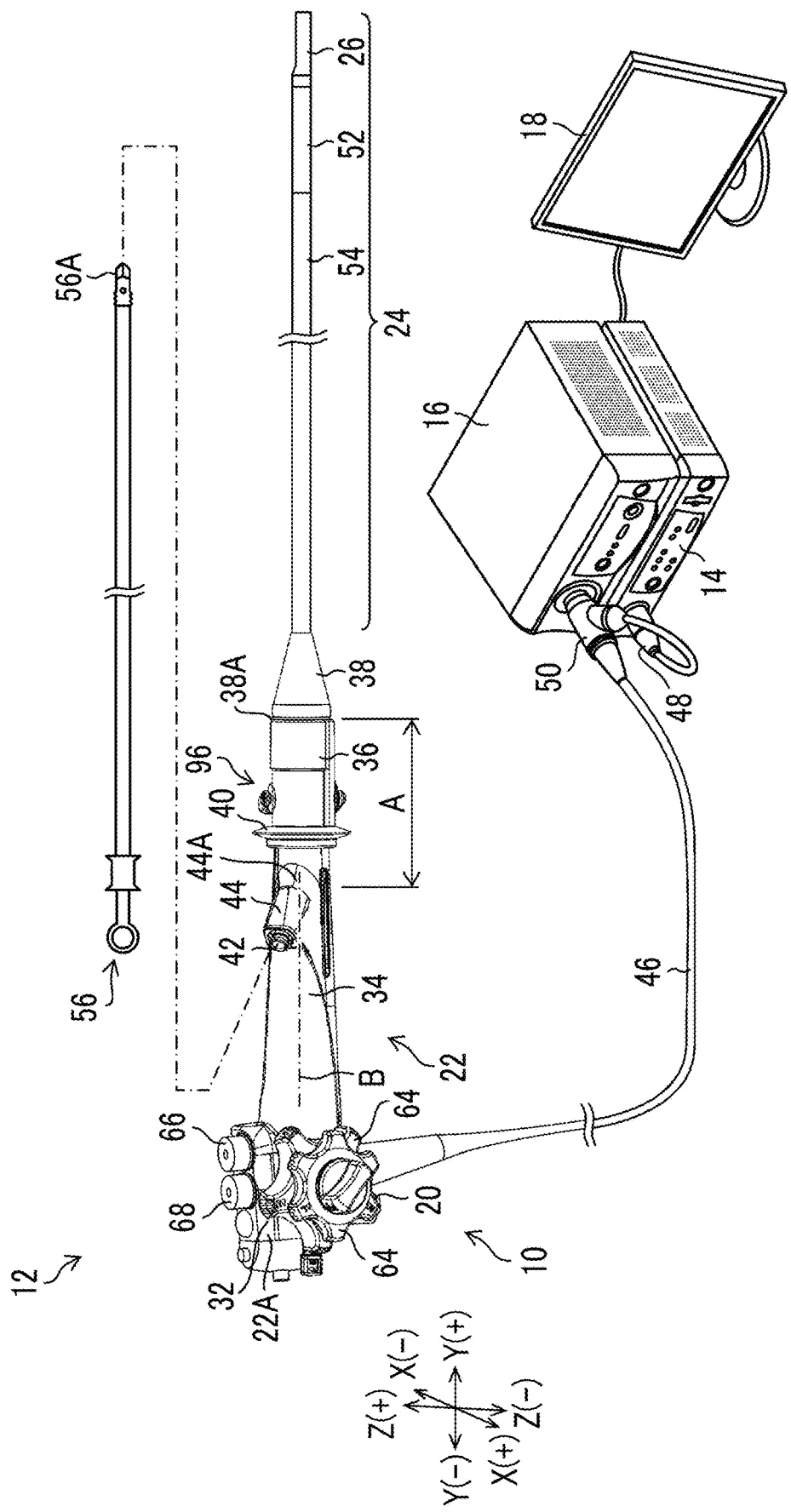
FIG. 1 is a diagram showing the configuration of an endoscope system comprising an endoscope according to an embodiment.

FIG. 1 is a diagram showing the configuration of an endoscope system 12 comprising an endoscope 10 according to an embodiment of the invention. The endoscope system 12 comprises an endoscope 10, a processor device 14, a light source device 16, and a display 18. A treatment tool 56 to be used for the endoscope system 12 is also shown in FIG. 1.

The endoscope 10 comprises an operation unit 22 that comprises an elevating operation lever 20 as an operation member, and an insertion unit 24 that is provided on the distal end side of the operation unit 22.

Figure 2:
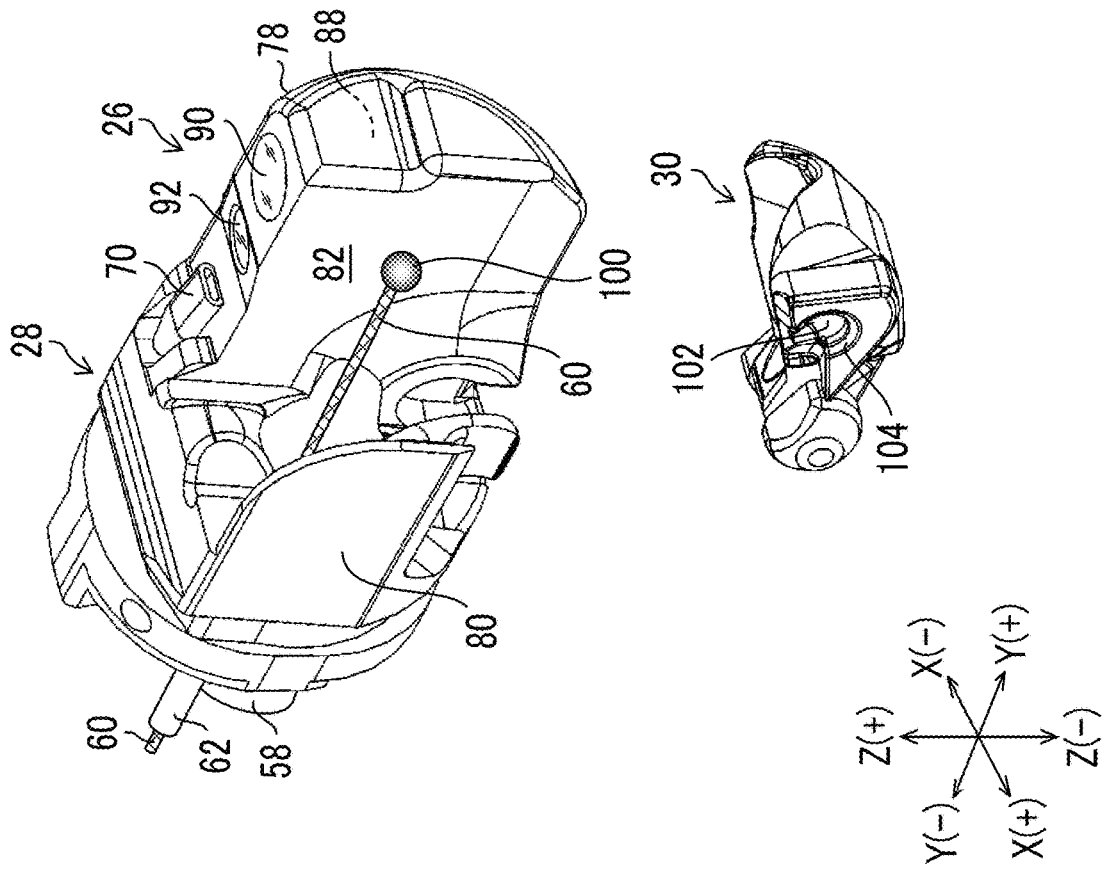
FIG. 2 is an exploded perspective view showing the configuration of a distal end part of an insertion unit.

FIG. 2 is an exploded perspective view showing the configuration of a distal end part 26 of the insertion unit 24, FIG. 3 is a perspective view of the distal end part 26 of which an elevator 30 is positioned at an elevated position, and FIG. 4 is a perspective view of the distal end part 26 of which the elevator 30 is positioned at a fallen position. Further, FIG. 5 is a perspective view of the distal end part 26 of which the elevator 30 is positioned at an attachment/detachment position. The attachment/detachment position means a position where the elevator 30 is rotated toward the fallen position from the elevated position, is rotated from the fallen position in the same direction, and goes beyond the fallen position. This attachment/detachment position will be described later. As shown in FIGS. 2 to 5, the distal end part 26 of the insertion unit 24 is provided with a distal end member 28 and the elevator 30 is mounted on the distal end member 28.

In the following description, a Z(+) direction in FIGS. 1 to 5 is referred to as an upward direction and a Z(−) direction is referred to as a downward direction. Further, an X(+) direction is referred to as a right direction and an X(−) direction is referred to as a left direction. Furthermore, a Y(+) direction is referred to as a direction toward a distal end side and a Y(−) direction is referred to as a direction toward a proximal end side.

Returning to FIG. 1, the operation unit 22 includes an operation unit body 32 that is provided with the elevating operation lever 20, a grip part 34 that is connected to the operation unit body 32, and an extending part 36 that extends from the grip part 34 toward the distal end side. The proximal end portion of the insertion unit 24 is connected to the distal end side of the extending part 36 through a bending-proof pipe 38. The grip part 34 is a part that is to be gripped by an operator during the operation of the endoscope 10.

The extending part 36 is a part corresponding to a non-grip region which extends toward the distal end side from the distal end portion of the grip part 34 and on which a movable member 96 (see FIG. 9) connected to an elevating operation mechanism 120 (FIGS. 21 and 22) is provided. Specifically, a region A from a distal end portion 44A of a convex mount portion 44 for a treatment tool inlet 42, which is provided at the grip part 34, up to a proximal end portion 38A of the bending-proof pipe 38 corresponds to the extending part 36. An annular flange 40 is provided in the region A of the extending part 36. The elevating operation mechanism 120 and the movable member 96 will be described later.

The operation unit body 32 of the operation unit 22 is provided with a universal cord 46. A light source connector 50 is provided on the distal end side of the universal cord 46, and is connected to the light source device 16. Further, an electrical connector 48 is provided on the light source connector 50 so as to branch, and is connected to the processor device 14.

The insertion unit 24 is adapted so that the distal end part 26, a bendable part 52, and a soft part 54 are connected from the distal end side toward the proximal end side.

The following components are provided in the insertion unit 24. That is, components, such as a treatment tool channel 58, an elevating operation wire 60 (hereinafter referred to as a wire 60), an elevating operation wire channel 62 (hereinafter referred to as a wire channel 62), a light guide (not shown), an air/water supply tube (not shown), angle wires (not shown), and a signal cable (not shown), are provided in the insertion unit 24. The treatment tool channel 58 guides a distal end portion 56A of the treatment tool 56 shown in FIG. 1 to the distal end member 28 shown in FIG. 2, the wire 60 is used to perform an operation for changing the lead-out direction of the distal end portion 56A of the treatment tool 56 led out of the distal end member 28, the wire channel 62 guides the distal end portion of the wire 60 to the distal end member 28, and the light guide (not shown) guides illumination light supplied from the light source device 16 shown in FIG. 1 to the distal end member 28 shown in FIG. 2.

Returning to FIG. 1, the operation unit 22 is formed in a substantially cylindrical shape as a whole and has a cylinder axis B extending in a Y(+)-Y(−) direction. A pair of angle knobs 64 and 64 used to perform an operation for bending the bendable part 52 is disposed on one side surface 22A that is positioned on one side of a vertical cross section of the operation unit 22 including the cylinder axis B. The pair of angle knobs 64 and 64 are provided on the same axis so as to be rotationally movable.

The bendable part 52 includes a structure that is formed of a plurality of angle rings (not shown) connected to each other so as to be rotationally movable. The outer periphery of this structure is covered with a tubular mesh body woven with metal wires and the outer peripheral surface of the mesh body is covered with a tubular covering made of rubber, so that the bendable part 52 is formed. For example, four angle wires (not shown) are provided from the bendable part 52 having this configuration to the angle knobs 64 and 64 and these angle wires are pushed or pulled by the rotational moving operation of the angle knobs 64 and 64, so that the bendable part 52 is vertically and laterally bent.

The soft part 54 includes a spiral pipe (not shown) formed of a thin belt-like metal plate that has elasticity and is spirally wound. The outside of the spiral pipe is covered with a tubular mesh body woven with metal wires and the outer peripheral surface of the mesh body is covered with a tubular covering consisting of a resin, so that the soft part 54 is formed.

Figure 6:
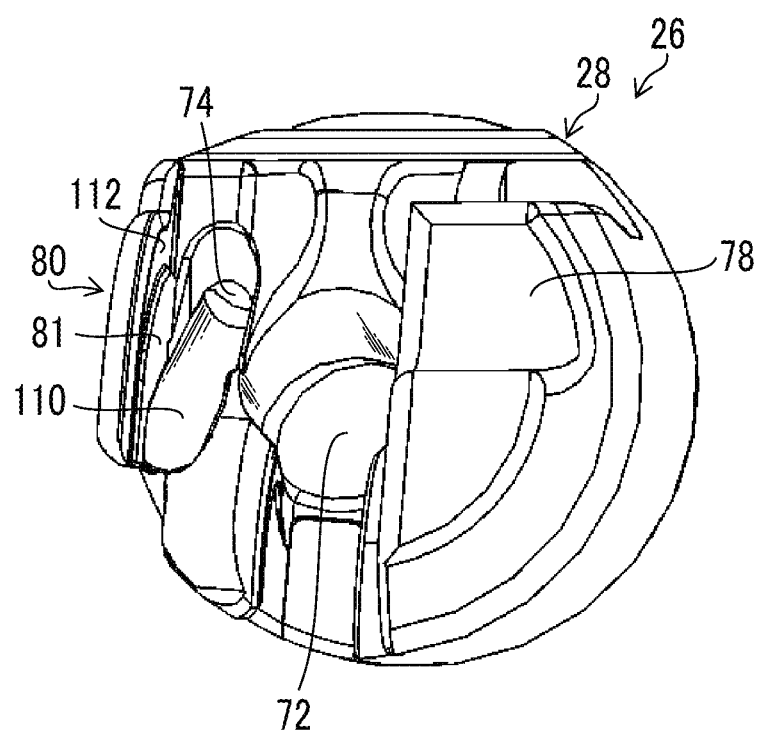
FIG. 6 is a front view of a distal end member in a case where the distal end member is viewed toward a proximal end side from a distal end side.

An air/water supply button 66 and a suction button 68 are provided on the operation unit body 32 side by side. In a case where the air/water supply button 66 is operated, air and water can be jetted from an air/water supply nozzle 70 provided on the distal end member 28 shown in FIG. 2. Further, in a case where the suction button 68 shown in FIG. 1 is operated, body fluid, such as blood, can be sucked from a suction port that is provided on the distal end member 28 shown in FIG. 2 and also functions as a treatment tool outlet 72 (see FIG. 6). FIG. 6 is a front view of the distal end member 28 in a case where the distal end member 28 is viewed toward the proximal end side from the distal end side.

Furthermore, the grip part 34 of the operation unit 22 shown in FIG. 1 is provided with a treatment tool inlet 42 into which the treatment tool 56 is to be introduced. The treatment tool 56, which is introduced from the treatment tool inlet 42 so that the distal end portion 56A becomes a leading end, is inserted into the treatment tool channel 58 of FIG. 2 inserted into the insertion unit 24 and is led out of the treatment tool outlet 72 shown in FIG. 6 to the outside.

Further, the elevating operation lever 20 is rotatably provided on the same axis as the angle knobs 64 and 64 on one side surface 22A of the operation unit 22 shown in FIG. 1. The elevating operation lever 20 is operated to rotate by the hand of an operator gripping the grip part 34. In a case where the elevating operation lever 20 is operated to rotate, the wire 60 shown in FIG. 2 is pushed or pulled by the elevating operation mechanism 120 (see FIGS. 21 and 22) that operates in conjunction with the rotating operation of the elevating operation lever 20. Accordingly, the attitude of the elevator 30, which is connected to the distal end portion of the wire 60, is changed between the elevated position shown in FIG. 3 and the fallen position shown in FIG. 4.

The endoscope 10 according to the embodiment having the above-mentioned configuration is a side-viewing endoscope used as a duodenoscope, and the insertion unit 24 is inserted into an object to be examined through an oral cavity. The insertion unit 24 is inserted into the duodenum from the gullet through the stomach, so that treatment, such as predetermined examination or predetermined therapy, is performed.

A pair of biopsy forceps, which includes a cup provided at the distal end portion 56A thereof and capable of being used to collect body tissue, has been exemplified as the treatment tool 56 in the embodiment, but the treatment tool 56 is not limited thereto. For example, a treatment tool, such as a contrast tube or a knife for endoscopic sphincterotomy (EST), can be exemplified as another treatment tool.

Next, the distal end part 26 will be described.

As shown in FIG. 2, the distal end part 26 includes the distal end member 28 and a cap member 76 that is attachably and detachably mounted on the distal end member 28. The cap member 76 is formed substantially in the shape of a tube of which the distal end side is sealed, and a substantially rectangular open window 76A is formed at a part of the outer peripheral surface of the cap member 76. In a case where the cap member 76 is mounted on the distal end member 28, the open window 76A of the cap member 76 communicates with the treatment tool outlet 72 (see FIG. 6) of the distal end member 28. Accordingly, the distal end portion 56A of the treatment tool 56 led out of the treatment tool outlet 72 is led out of the open window 76A to the outside.

Further, a position regulating member 77 is provided on the inner peripheral portion of the cap member 76 as shown in FIG. 5. The cap member 76 is disposed so as to face the elevator 30 in a case where the cap member 76 is mounted on the distal end member 28. In a case where the elevator 30 is in contact with the position regulating member 77, the elevator 30 is held at the attachment/detachment position shown in FIG. 5. The position regulating member 77 may be formed integrally with the cap member 76, or may be formed separately and bonded to the inner peripheral portion of the cap member 76.

The cap member 76 is made of an elastic material, for example, a rubber material, such as fluororubber or silicone rubber, or a resin material, such as polysulfone, and an engaging portion (not shown) to be engaged with a groove (not shown) formed on the distal end member 28 is provided on the proximal end side of the cap member 76. The engaging portion is engaged with the groove of the distal end member 28, so that the cap member 76 is mounted on the distal end member 28. Furthermore, after treatment using the endoscope 10 ends, the cap member 76 is detached from the distal end member 28, is washed and disinfected or sterilized or is discarded as a disposable.

The distal end member 28 is made of a metal material having corrosion resistance. Further, a partition wall 78 protruding toward the distal end side and a partition wall 80 facing the partition wall 78 are provided integrally with the distal end member 28.

As shown in FIG. 2, an elevator-housing chamber 82 housing the elevator 30 is formed between the partition walls 78 and 80. The treatment tool outlet 72 (see FIG. 6) out of which the treatment tool 56 is led to the outside is formed on the proximal end side of the elevator-housing chamber 82. The distal end portion of the treatment tool channel 58 (see FIG. 2) is connected to the treatment tool outlet 72.

The treatment tool channel 58 is inserted into the insertion unit 24 shown in FIG. 1. The proximal end portion of the treatment tool channel 58 is connected to a distal end pipe 202 of a branch pipe 200 (see FIG. 22) provided in the operation unit 22.

The branch pipe 200 has a well-known structure. The proximal end portion of the branch pipe 200 branches into two pipe lines 204 and 206, and the treatment tool inlet 42 is formed at the proximal end of one pipe line 204. Accordingly, the distal end portion 56A of the treatment tool 56 introduced into the pipe line 204 from the treatment tool inlet 42 is inserted into the treatment tool channel 58 and is led out of the treatment tool outlet 72 shown in FIG. 6 to the elevator-housing chamber 82 shown in FIG. 2. Then, the lead-out direction of the distal end portion 56A of the treatment tool 56 led to the elevator-housing chamber 82 is changed according to the attitude of the elevator 30, which is disposed in the elevator-housing chamber 82, between the elevated position and the fallen position. Further, the distal end of a suction pipe 208 sucking body fluid, such as blood, is connected to the proximal end of the other pipe line 206 of the branch pipe 200 shown in FIG. 20.

FIG. 7 is an enlarged perspective view of the elevator 30. As shown in FIG. 7, a guide surface 30A is provided on the upper surface of the elevator 30. The distal end portion 56A of the treatment tool 56 shown in FIG. 1 is led out of the open window 76A of the cap member 76 shown in FIG. 2 to the outside along the guide surface 30A.

As shown in FIG. 7, rotational movement shaft portions 84 and 86 are provided on both side surfaces of the base portion 30B of the elevator 30. The axial direction of these rotational movement shaft portions 84 and 86 is set to an X(+)-X(−) direction shown in FIG. 2 in a case where the elevator 30 is mounted on the distal end member 28 shown in FIG. 2. Further, flat notch surfaces 84A and 86B are formed on the peripheral surfaces of the rotational movement shaft portions 84 and 86.

Figure 8:
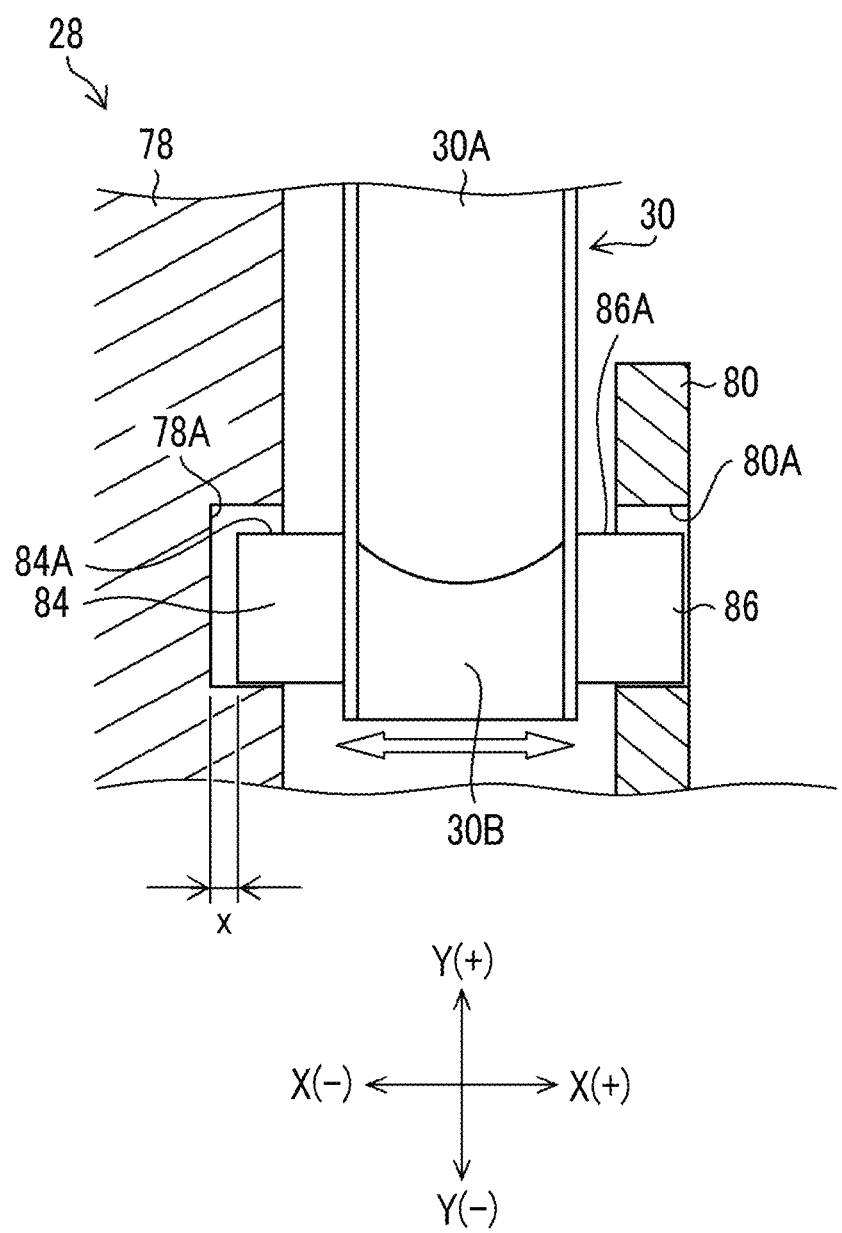
FIG. 8 is a cross-sectional view of main portions showing a structure for mounting the elevator on the distal end member.

FIG. 8 is a cross-sectional view of main portions showing a structure for mounting the elevator 30 on the distal end member 28.

As shown in FIG. 8, the axes of the rotational movement shaft portions 84 and 86 are disposed on the same axis through the base portion 30B of the elevator 30. The rotational movement shaft portion 84 is fitted to a recessed bearing portion 78A of the partition wall 78 so as to be rotationally movable, and the rotational movement shaft portion 86 is fitted to a recessed bearing portion 80A of the partition wall 80 so as to be rotationally movable. Furthermore, the rotational movement shaft portions 84 and 86 are mounted in the bearing portions 78A and 80A while having a predetermined clearance x in the axial direction of the rotational movement shaft portions 84 and 86. In a case where the rotational movement shaft portions 84 and 86 are biased to one side using the clearance x, a part of one of the bearing portions 78A and 80A is exposed to the outside. Since a brush can be easily inserted into the exposed portion, the washability of the bearing portions 78A and 80A is improved. Moreover, since the flat notch surfaces 84A and 86B are formed on the peripheral surfaces of the rotational movement shaft portions 84 and 86 as shown in FIG. 7, a brush can be easily inserted into gaps between the notch surfaces 84A and 86B and the inner peripheral surfaces of the bearing portions 78A and 80A. Accordingly, the washability of the bearing portions 78A and 80A is further improved.

As shown in FIG. 2, an optical system-housing chamber 88 is provided in the partition wall 78. An illumination window 90 and an observation window 92 are provided at the upper portion of the optical system-housing chamber 88 so as to be adjacent to each other, and the air/water supply nozzle 70 directed to the observation window 92 is provided on the distal end member 28. The air/water supply nozzle 70 is connected to an air/water supply device (not shown) through an air/water supply tube (not shown) inserted into the insertion unit 24, and air or water is jetted toward the observation window 92 from the air/water supply nozzle 70 in a case where the air/water supply button 66 of the operation unit 22 shown in FIG. 1 is operated. Accordingly, the observation window 92 is washed.

Further, an illumination unit (not shown) and an image pickup unit (not shown) are housed in the optical system-housing chamber 88. The illumination unit comprises an illumination lens (not shown) that is installed in the illumination window 90, and a light guide (not shown) that is disposed so that the distal end surface of the light guide faces the illumination lens. The light guide is disposed in the universal cord 46 from the insertion unit 24 shown in FIG. 1 through the operation unit 22, and the proximal end of the light guide is connected to the light source device 16 through the light source connector 50. Accordingly, illumination light generated from the light source device 16 is transmitted through the light guide and is applied to the outside from the illumination window 90.

The above-mentioned image pickup unit comprises an image pickup optical system (not shown) that is provided in the observation window 92 and a complementary metal oxide semiconductor (CMOS) or charge coupled device (CCD) image pickup element (not shown). The image pickup element is connected to the processor device 14 through a signal cable (not shown) inserted into the insertion unit 24 shown in FIG. 1. After image pickup signals of a subject image obtained by the image pickup unit are output to the processor device 14 through the signal cable and are subjected to image processing, the image pickup signals are displayed on the display 18 as a subject image.

Although the above description is repeated, the distal end portion of the wire 60 is led to the outside of an outlet 74 (see FIG. 6) and is connected to the elevator 30 as shown in FIG. 2. Further, the proximal end portion of the wire 60 is disposed outside an inlet 94 provided on the operation unit 22 as shown in FIG. 9, and is connected to the movable member 96.

Figure 9:
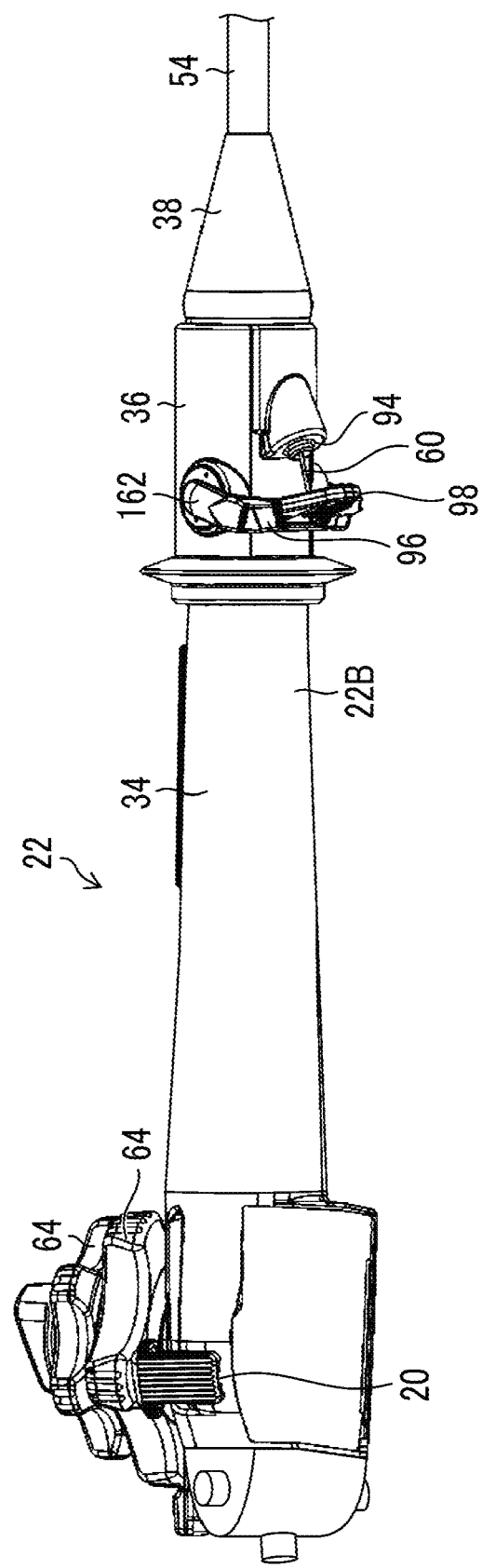
FIG. 9 is a perspective view of an operation unit.

FIG. 9 is a perspective view of the operation unit 22, and is a perspective view showing the other side surface 22B facing one side surface 22A of the operation unit 22 shown in FIG. 1.

According to FIG. 9, the extending part 36 of the operation unit 22 is provided with the inlet 94. A mounting member 98 is provided at the proximal end of the wire 60 disposed outside the inlet 94, and is attachably and detachably mounted in an engaging hole (to be described later) of the movable member 96. Accordingly, the proximal end portion of the wire 60 is connected to the movable member 96.

The operation unit 22 is provided with the movable member 96. The movable member 96 is disposed to be exposed to the outside of the operation unit 22, and is operated in conjunction with the rotating operation of the elevating operation lever 20 by the elevating operation mechanism 120 (see FIGS. 21 and 22). The movable member 96 is a driven lever that is rotated in conjunction with the rotating operation of the elevating operation lever 20.

The elevating operation mechanism 120 is a mechanism that is disposed in the operation unit 22 and causes the movable member 96 to operate in conjunction with the operation of the elevating operation lever 20. Accordingly, in a case where the elevating operation lever 20 is operated to rotate, the movable member 96 is operated through the elevating operation mechanism 120 and the wire 60 (see FIG. 2) connected to the movable member 96 is pushed or pulled.

Next, a connection structure for detachably connecting the distal end portion of the wire 60 to the elevator 30 will be described.

Returning to FIG. 2, an engaging portion 100 is provided at the distal end portion of the wire 60. Further, the elevator 30 is provided with a contact portion 101 as shown in FIG. 7. The engaging portion 100 led out of the outlet 74 (see FIG. 6) is in contact with the contact portion 101. The engaging portion 100 is in contact with the contact portion 101, so that a rotational moving force acting in a fallen direction is applied to the elevator 30.

Further, the elevator 30 is provided with a housing portion 102 that is detachably engaged with the engaging portion 100. An opening 104 is formed on the side of the housing portion 102 corresponding to the X(+) direction. The engaging portion 100 is engaged with the housing portion 102 through the opening 104, so that the distal end portion of the wire 60 is connected to the elevator 30.

Furthermore, the elevator 30 is provided with a guide portion 106 for engagement that guides the engaging portion 100 to the opening 104. The guide portion 106 for engagement includes a guide passage 108 that guides the engaging portion 100 in the X(+) direction where the engaging portion 100 is separated from the opening 104.

In the embodiment, the engaging portion 100 is a sphere and the housing portion 102 is a spherical concave portion that houses the engaging portion 100 formed of a sphere. The shapes of the engaging portion 100 and the housing portion 102 are not limited to the above-mentioned shapes. However, in a case where the engaging portion 100 is formed of a sphere and the housing portion 102 is formed of a spherical concave portion, sliding resistance between the engaging portion 100 and the housing portion 102 generated due to an operation of pushing or pulling the wire 60 can be reduced. Accordingly, an operation for pushing or pulling the wire 60 can be smoothly performed.

Figure 11:
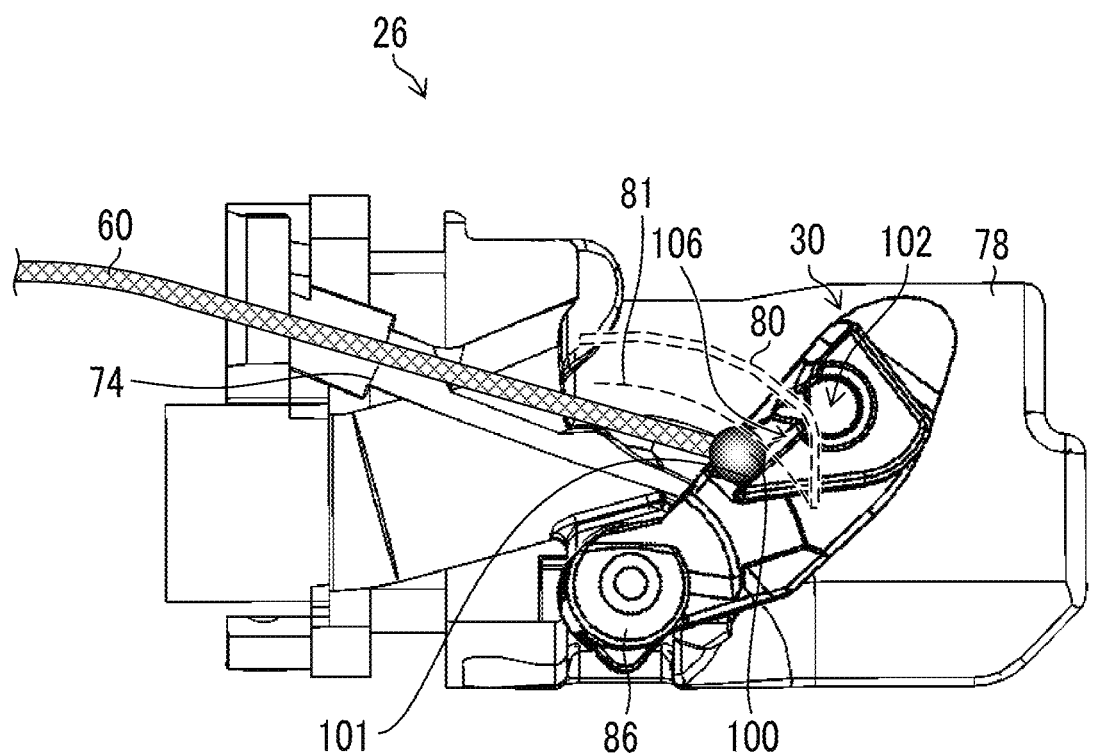
FIG. 11 is a diagram illustrating a state where the engaging portion is in contact with the contact portion of the elevator positioned at the fallen position.
Figure 12:
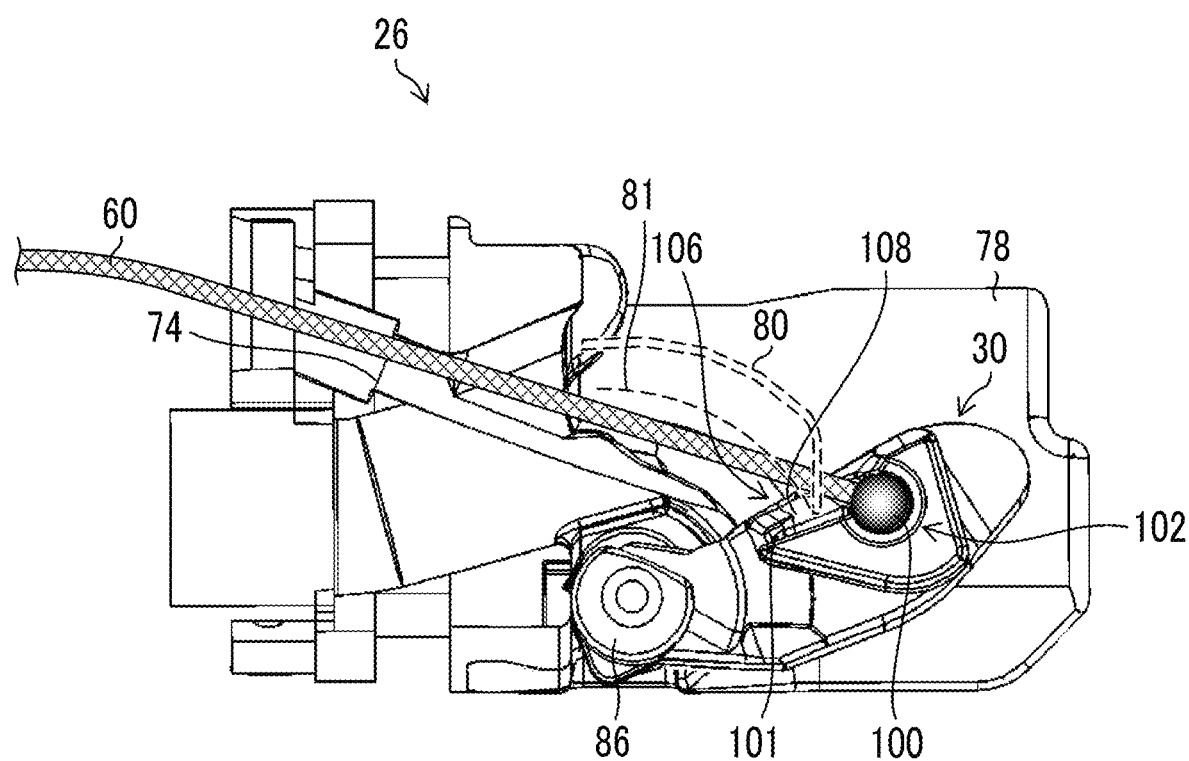
FIG. 12 is a diagram illustrating that the engaging portion is housed in a housing portion of the elevator positioned at the attachment/detachment position.

As shown in FIG. 6, the partition wall 80 is provided with a wall portion 81. The wall portion 81 is provided at a position adjacent to the elevator 30 shown in FIGS. 3 and 4. The wall portion 81 is provided at a position facing the movement trajectory of the engaging portion 100 in a case where the elevator 30 is moved between the elevated position shown in FIG. 10 and the fallen position shown in FIG. 11 in a state where the engaging portion 100 is in contact with the contact portion 101 as shown in FIG. 10. In a state where the engaging portion 100 is in contact with the contact portion 101, the wall portion 81 regulates the movement of the engaging portion 100 in the X(−) direction where the engaging portion 100 enters the opening 104 in a case where the elevator 30 is present between the elevated position shown in FIG. 10 and the fallen position shown in FIG. 11 and allows the movement of the engaging portion 100 in the X(−) direction where the engaging portion 100 enters the opening 104 in a case where the elevator 30 is present between the fallen position shown in FIG. 11 and the attachment/detachment position shown in FIG. 12.

Figure 13:
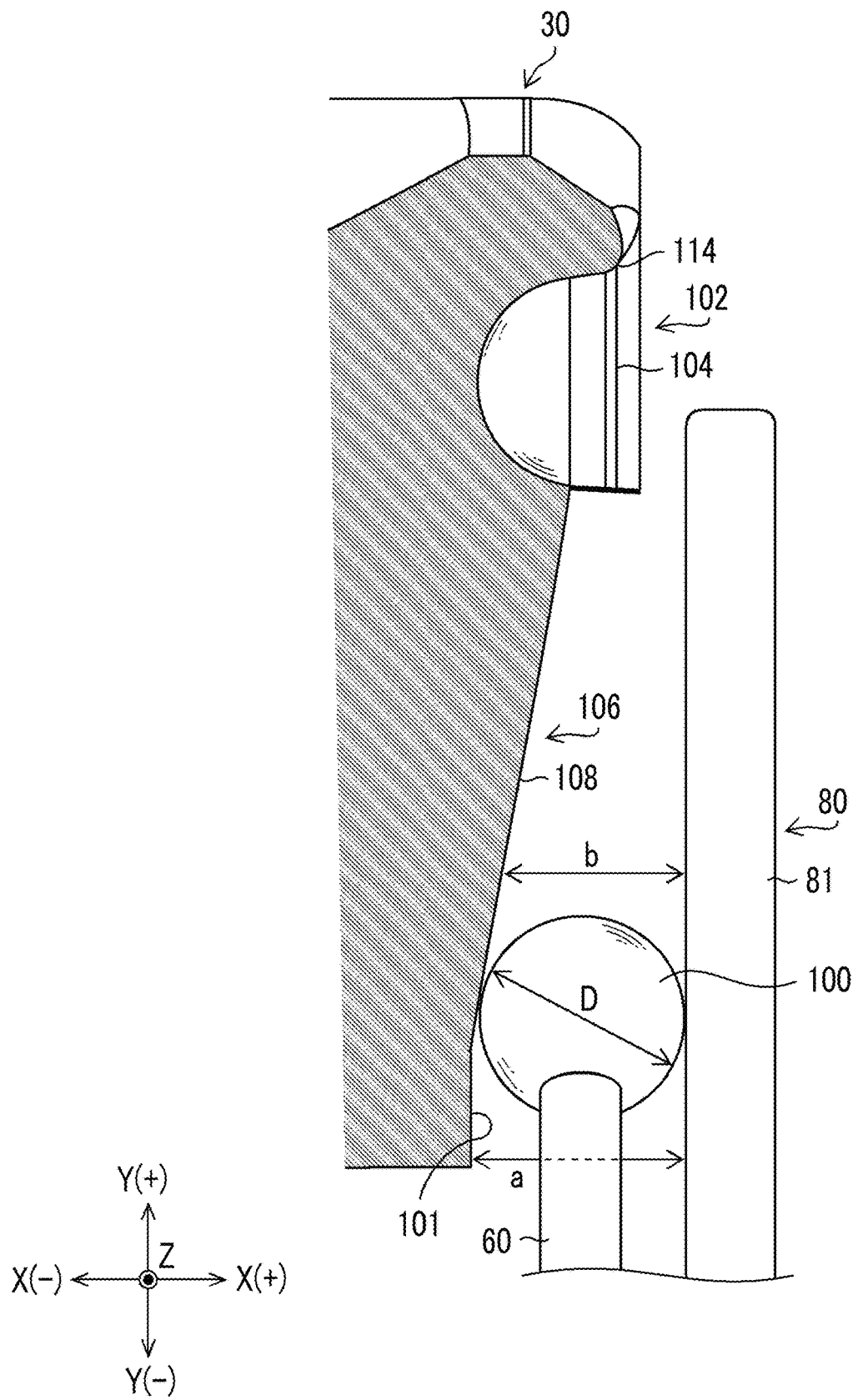
FIG. 13 is a diagram illustrating a positional relationship between the elevator and a partition wall.

That is, as shown in FIG. 13, a gap a in the X(+)-X(−) direction between the surface of the contact portion 101 and the surface of the wall portion 81 facing the contact portion 101 is set to be equal to the diameter D of the engaging portion 100. However, a gap b in the X(+)-X(−) direction between the surface of the guide portion 106 for engagement and the surface of the wall portion 81 facing the guide portion 106 for engagement is set to be smaller than the diameter D of the engaging portion 100. For this reason, even though the elevator 30 is present at any position between the elevated position and the fallen position, a state where the engaging portion 100 led out of the outlet 74 (see FIG. 6) is in contact with the contact portion 101 is maintained. Accordingly, the contact portion 101 can apply a rotational moving force acting in the fallen direction to the elevator 30.

Figure 14:
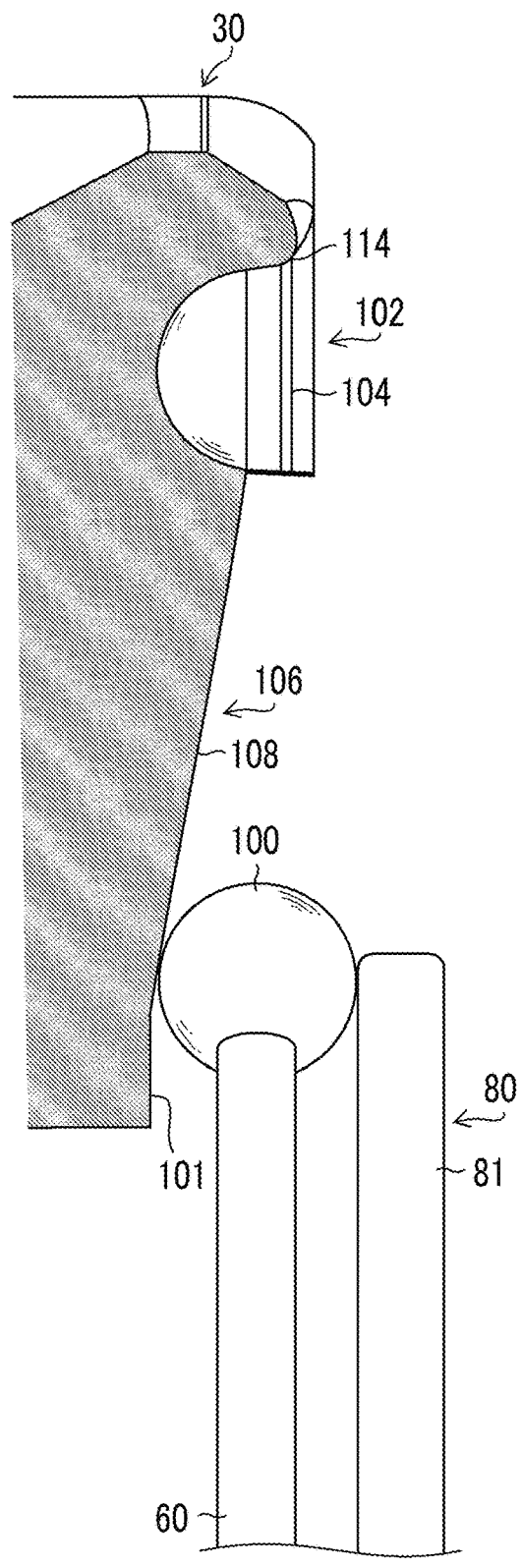
FIG. 14 is a diagram illustrating a positional relationship between the elevator gone beyond the fallen position and the partition wall.
Figure 16:
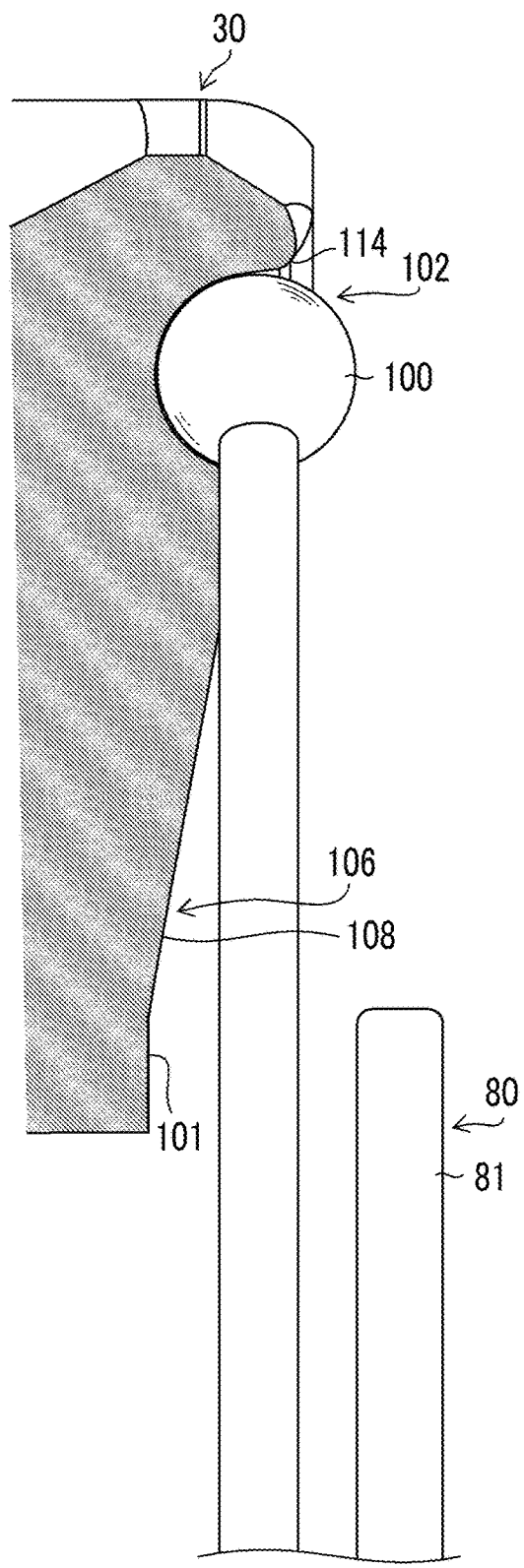
FIG. 16 is a diagram illustrating that the engaging portion is engaged with the housing portion.

On the other hand, in a case where the elevator 30 goes beyond the fallen position from the elevated position due to an operation of introducing the wire 60, the wall portion 81 is not present at a position facing the guide portion 106 for engagement. For this reason, the engaging portion 100 is pushed toward the guide portion 106 for engagement from the contact portion 101 as shown in FIG. 14 and is guided toward the opening 104 of the housing portion 102 along the guide passage 108 as shown in FIG. 15. Then, the elevator 30 is moved toward the attachment/detachment position shown in FIG. 12 in conjunction with an operation for pushing the engaging portion 100. After that, in a case where the elevator 30 is stopped at the attachment/detachment position where the elevator 30 is in contact with the position regulating member 77 (see FIG. 5), the engaging portion 100 passes through the guide passage 108 and the engaging portion 100 is engaged with the housing portion 102 through the opening 104 as shown in FIG. 16 due to the elastic restoring force of the wire 60 shown by an arrow c of FIG. 15.

Therefore, according to the endoscope 10 of the embodiment, even though the elevator 30 is present at any position between the elevated position and the fallen position, the engaging portion 100 of the wire 60 can be engaged with the housing portion 102 of the elevator 30 by only an operation for introducing the wire 60.

Figure 17:
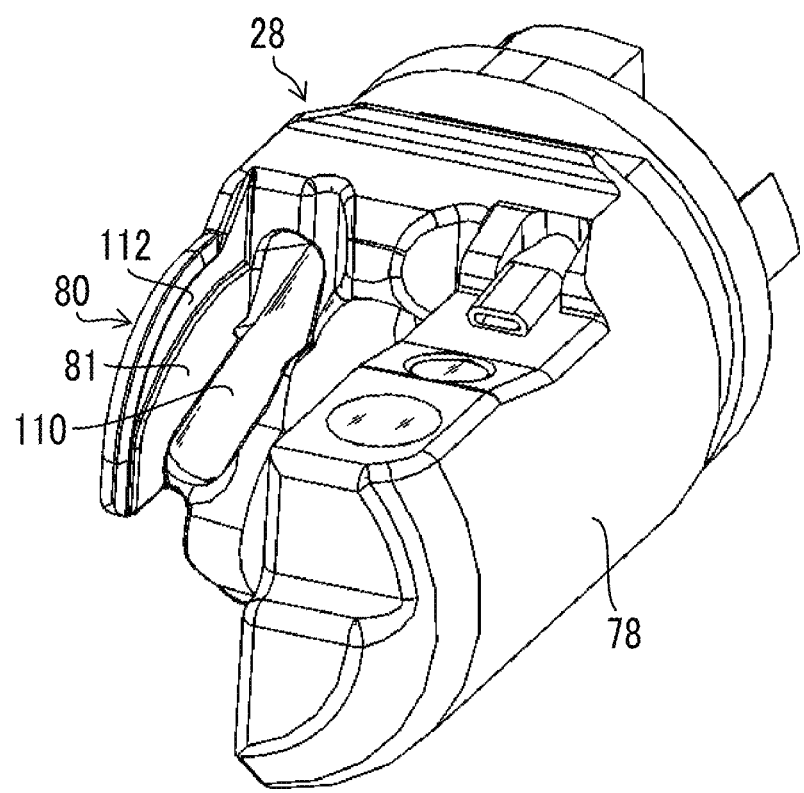
FIG. 17 is a perspective view of the distal end member.

Further, as shown in FIG. 6 and a perspective view of the distal end member 28 shown in FIG. 17, the distal end member 28 is provided with a wire guide portion 110. The wire guide portion 110 guides the engaging portion 100, which is led out of the outlet 74, to the contact portion 101. The wire guide portion 110 is formed of a groove having an arc-shaped cross section, and is formed so that the radius of curvature of the wire guide portion 110 is equal to the radius of the engaging portion 100. Accordingly, since the engaging portion 100 led out of the outlet 74 shown in FIG. 6 is guided toward the contact portion 101 while being in sliding contact with the wire guide portion 110, the engaging portion 100 can be reliably in contact with the contact portion 101 reliably. The shape of the wire guide portion 110 is not limited to the above-mentioned shape. For example, the wire guide portion 110 may be an arc-shaped groove of which the radius of curvature is larger than the radius of the engaging portion 100 or may be a groove having a rectangular cross section.

Figure 18:
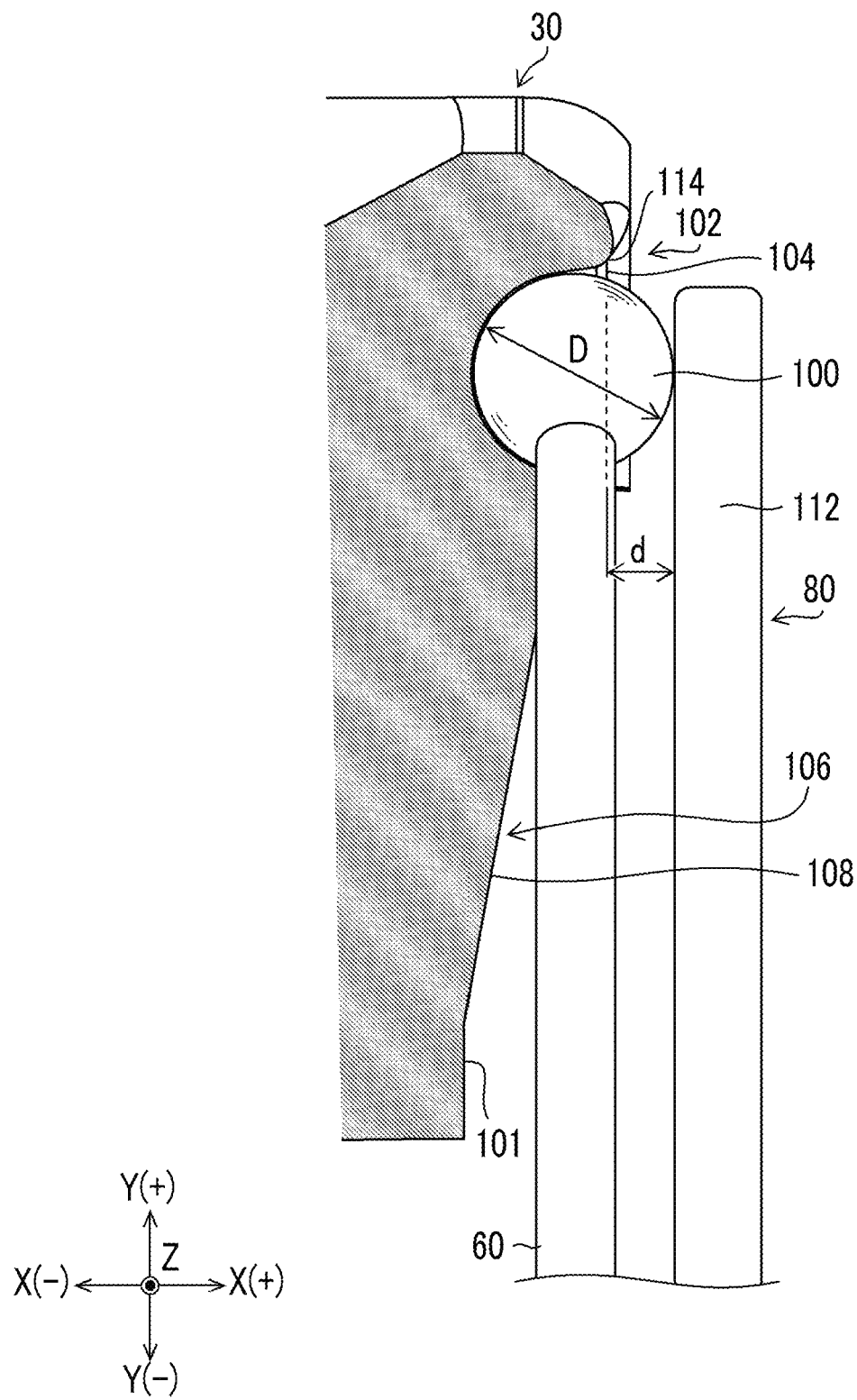
FIG. 18 is a diagram illustrating a positional relationship between the engaging portion and a retaining portion.

Furthermore, the partition wall 80 is provided with a retaining portion 112 as shown in FIG. 17. The retaining portion 112 is provided at a position facing the movement trajectory of the engaging portion 100 in a case where the elevator 30 is moved between the elevated position shown in FIG. 3 and the fallen position shown in FIG. 4 in a state where the engaging portion 100 is housed in the housing portion 102, and maintains a state where the housing portion 102 and the engaging portion 100 are engaged with each other. That is, since a gap d in the X(+)-X(−) direction between an open surface of the opening 104 and the surface of the retaining portion 112 facing the open surface of the opening 104 is set to be smaller than the diameter D of the engaging portion 100 as shown in FIG. 18, a state where the housing portion 102 and the engaging portion 100 are engaged with each other can be maintained between the elevated position shown in FIG. 3 and the fallen position shown in FIG. 4.

Next, a disengaging structure for disengaging the engaging portion 100 of the wire 60, which is engaged with the housing portion 102, from the housing portion 102 will be described.

As shown in FIGS. 13 to 16 and FIG. 18, an inclined surface 114 for disengagement, which is widened toward the outside of the opening 104, is formed on the housing portion 102. The inclined surface 114 for disengagement is formed on an inner surface, which corresponds to the lead-out direction (Y(+) direction) of the engaging portion 100, in the inner surface of the housing portion 102 close to the opening 104. The inclined surface 114 for disengagement functions as a surface that guides the engaging portion 100 to the outside of the opening 104 from the housing portion 102 in a case where the wire 60 is operated to be pushed in a state where the engaging portion 100 is engaged with the housing portion 102 and the elevator 30 is positioned at the attachment/detachment position.

Figure 19:
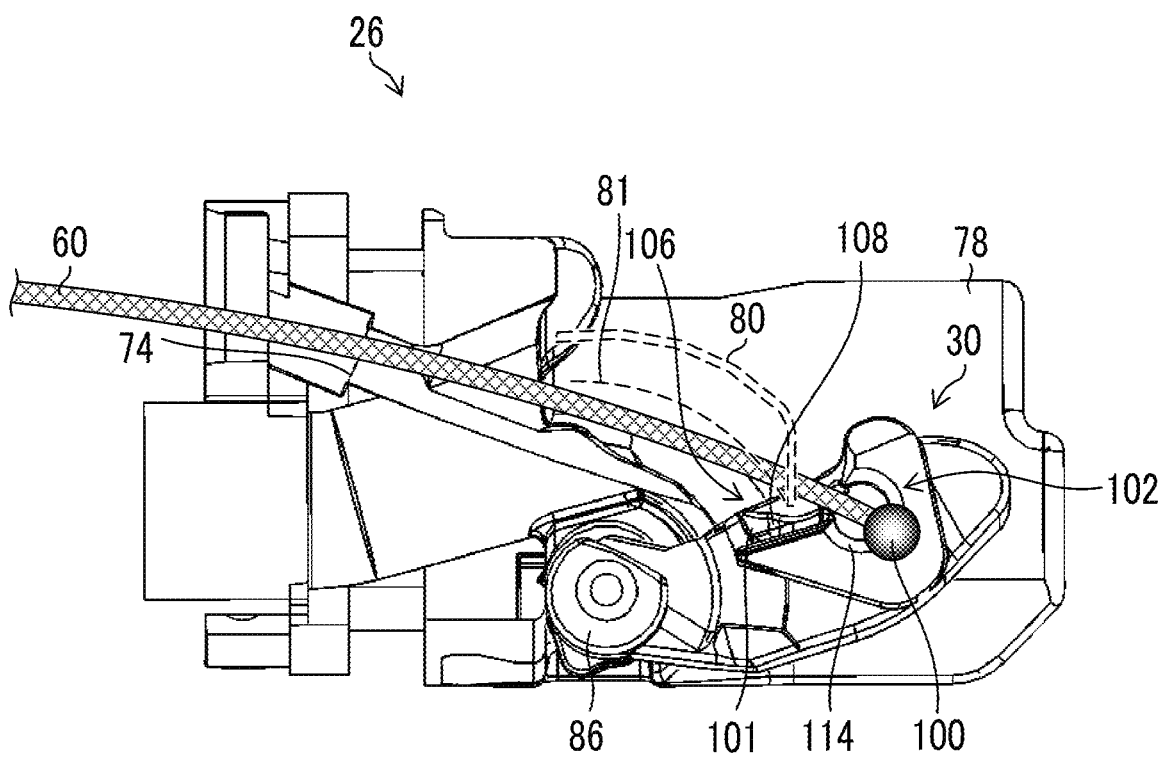
FIG. 19 is a diagram illustrating a positional relationship between the engaging portion and the elevator immediately before the engaging portion disengaged from the housing portion.

According to the disengaging structure having this configuration, in a case where the wire 60 is operated to be pushed after the elevator 30 is positioned at the attachment/detachment position shown in FIG. 19, the engaging portion 100 is guided to the inclined surface 114 for disengagement and is disengaged from the housing portion 102 to the outside of the opening 104. Accordingly, the engaging portion 100 engaged with the housing portion 102 can be easily disengaged from the housing portion 102. FIG. 19 is a diagram illustrating a positional relationship between the engaging portion 100 and the elevator 30 immediately before the engaging portion 100 is disengaged from the housing portion 102.

Figure 20:
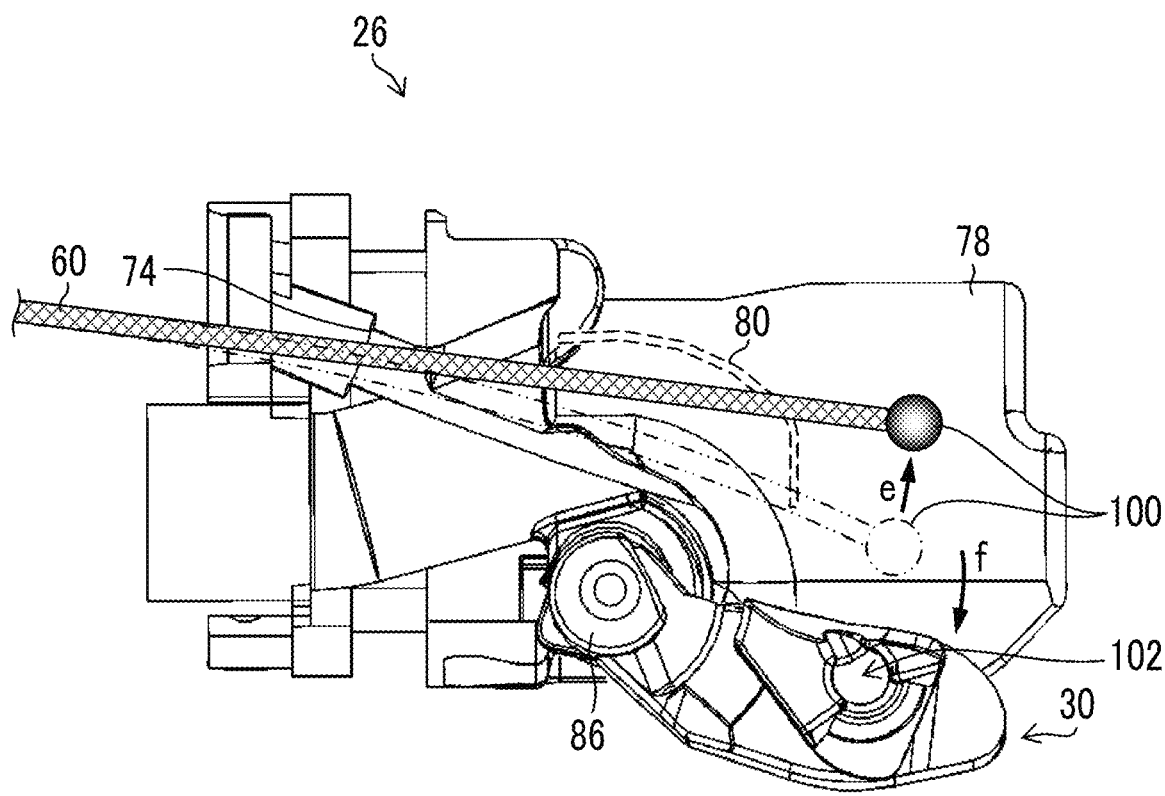
FIG. 20 is a diagram illustrating a positional relationship between the engaging portion and the elevator in a case where the engaging portion is disengaged from the housing portion.

FIG. 20 is a diagram illustrating a positional relationship between the engaging portion 100 and the elevator 30 in a case where the engaging portion 100 is disengaged from the housing portion 102. The direction of the engaging portion 100 is changed to a direction parallel to the Y(+) direction as shown by an arrow e due to the elastic restoring force of the wire 60. On the other hand, the elevator 30 moves rotationally in a Z(−) direction as shown by an arrow f due to its own weight. In a case where the cap member 76 shown in FIG. 5 is mounted on the distal end member 28, the elevator 30 is regulated to the attachment/detachment position by the position regulating member 77. Accordingly, the elevator 30 is held at the attachment/detachment position.

Next, the elevating operation mechanism 120 shown in FIGS. 21 and 22 will be described.

Figure 21:
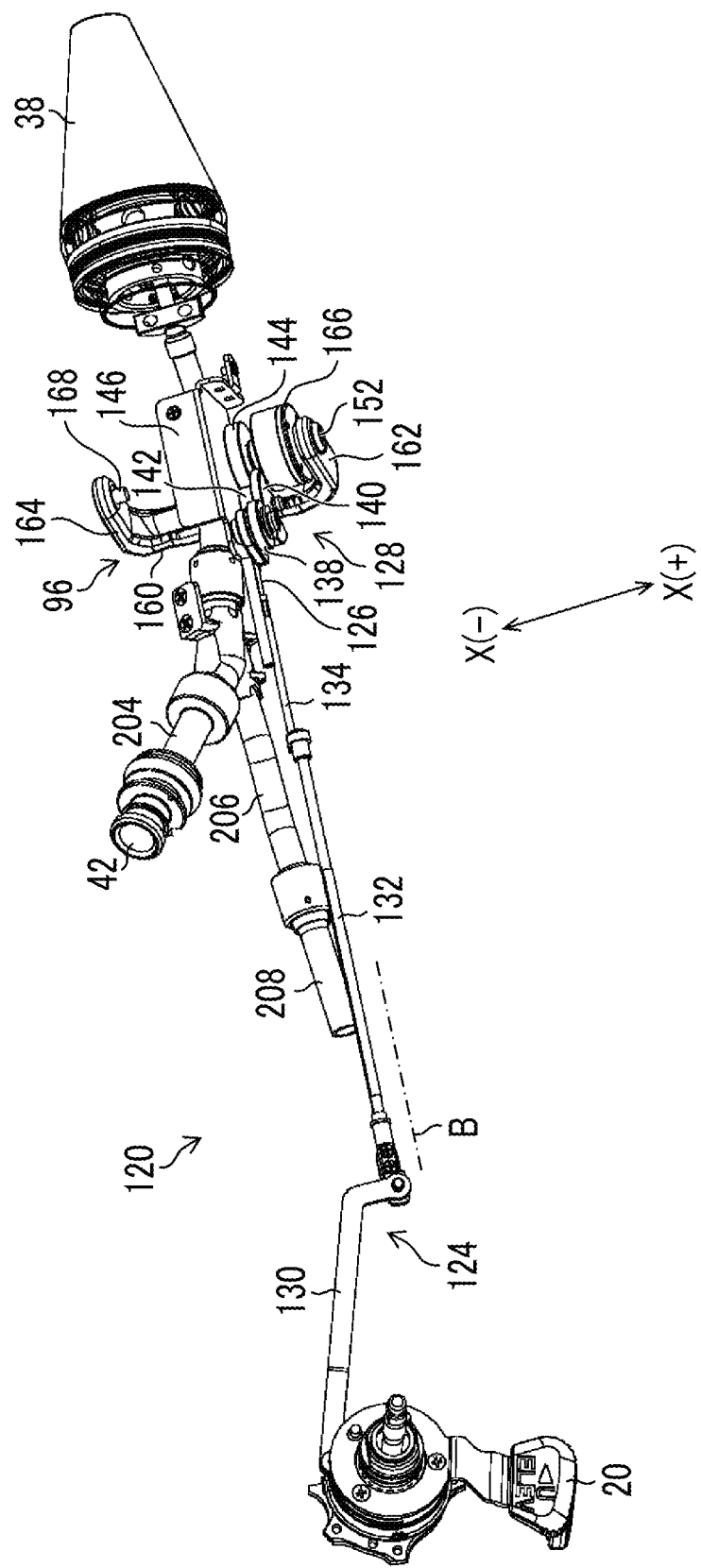
FIG. 21 is a diagram showing the entire configuration of an elevating operation mechanism.

FIG. 21 is a diagram showing the entire configuration of the elevating operation mechanism 120. Further, FIG. 22 is a side view of the elevating operation mechanism 120 shown in FIG. 21. In FIGS. 21 and 22, the exterior case (not shown) of the operation unit 22 will be omitted and the inside of the operation unit 22 is shown.

Figure 22:
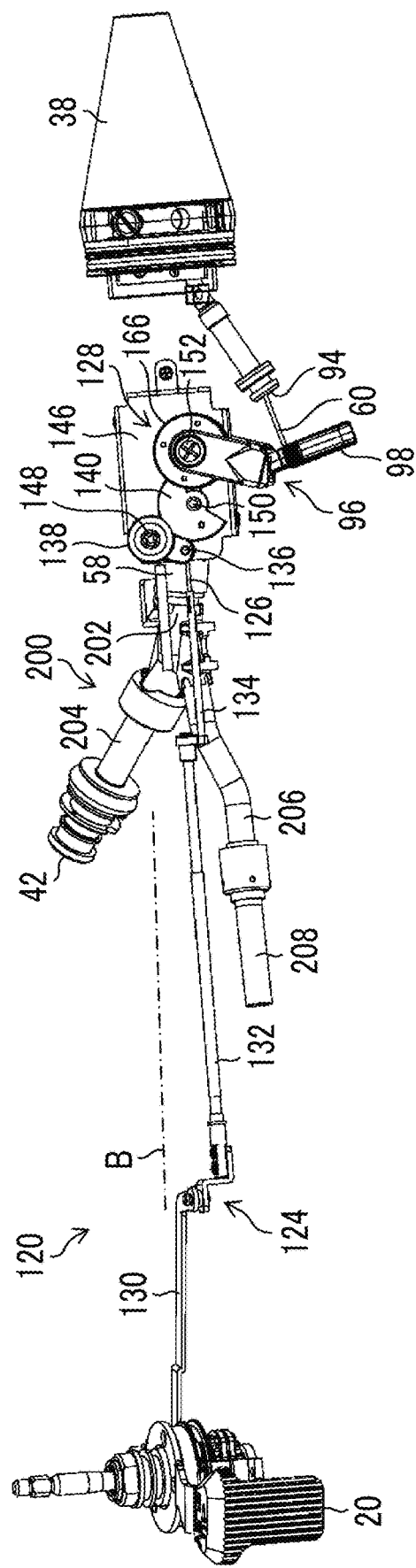
FIG. 22 is a side view of the elevating operation mechanism shown in FIG. 21.

As shown in FIGS. 21 and 22, the elevating operation mechanism 120 is provided in the operation unit 22. Specifically, the respective components of each part of the elevating operation mechanism 120 are provided in the operation unit 22 from the operation unit body 32 to the extending part 36.

Further, the elevating operation mechanism 120 is a power transmission mechanism that connects the elevating operation lever 20 to the movable member 96 and transmits the rotating operation of the elevating operation lever 20 to the movable member 96.

The elevating operation mechanism 120 comprises a first conversion mechanism 124 that converts the rotary motion of the elevating operation lever 20 into linear motion, a wire 126 that is linearly moved by the first conversion mechanism 124, and a second conversion mechanism 128 that converts the linear motion of the wire 126 into rotary motion to rotate the movable member 96.

The first conversion mechanism 124 comprises a crank member 130 of which the proximal end is connected to the elevating operation lever 20, a first slider 132 of which the proximal end is connected to the distal end of the crank member 130, and a second slider 134 of which the proximal end is connected to the distal end of the first slider 132.

The proximal end of the wire 126 is connected to the distal end of the second slider 134, and the distal end of the wire 126 is connected to the second conversion mechanism 128 including a speed reducer.

According to the first conversion mechanism 124 having the above-mentioned configuration, in a case where the elevating operation lever 20 is operated to rotate, the crank member 130, the first slider 132, and the second slider 134 are linearly moved along the cylinder axis B in conjunction with the rotating operation of the elevating operation lever 20. Accordingly, the wire 126 is linearly moved along the cylinder axis B, and the linear motion of the wire 126 is transmitted to the second conversion mechanism 128.

The second conversion mechanism 128 comprises a lever 136, a first gear 138, a second gear 140, a third gear 142, and a fourth gear 144. The first gear 138, the second gear 140, the third gear 142, and the fourth gear 144 form the speed reducer.

The lever 136 is rotatably supported on a bracket 146 through a shaft part 148, and the distal end of the wire 126 is connected to the lever 136. Accordingly, the lever 136 is rotated about the shaft part 148 by the linear motion of the wire 126.

The first gear 138 is provided integrally with the lever 136 and is rotated about the shaft part 148. The second gear 140 meshes with the first gear 138, and is rotatably supported on the bracket 146 through a shaft part 150. The third gear 142 is provided integrally with the second gear 140 and is provided on the same axis as the second gear 140. The fourth gear 144 is provided on the same axis as a drive shaft part 152 of the movable member 96, and is rotatably supported on the bracket 146 through the drive shaft part 152 together with the movable member 96. The third gear 142 meshes with the fourth gear 144.

Therefore, according to the second conversion mechanism 128 having the above-mentioned configuration, in a case where the linear motion of the wire 126 is transmitted to the lever 136, the first gear 138 is operated to rotate together with the lever 136 and the rotating operation of the first gear 138 is transmitted to the fourth gear 144 through the second and third gears 140 and 142. As a result, the fourth gear 144 is rotated. Accordingly, the movable member 96 integrated with the fourth gear 144 is rotated about the drive shaft part 152.

Therefore, according to the elevating operation mechanism 120 having the above-mentioned configuration, the rotating operation of the elevating operation lever 20 can be transmitted to the movable member 96 through the first conversion mechanism 124, the wire 126, and the second conversion mechanism 128. Accordingly, the movable member 96 is rotated about the drive shaft part 152.

Next, a positional relationship between the elevating operation lever 20 and the movable member 96 will be described.

Figure 24:
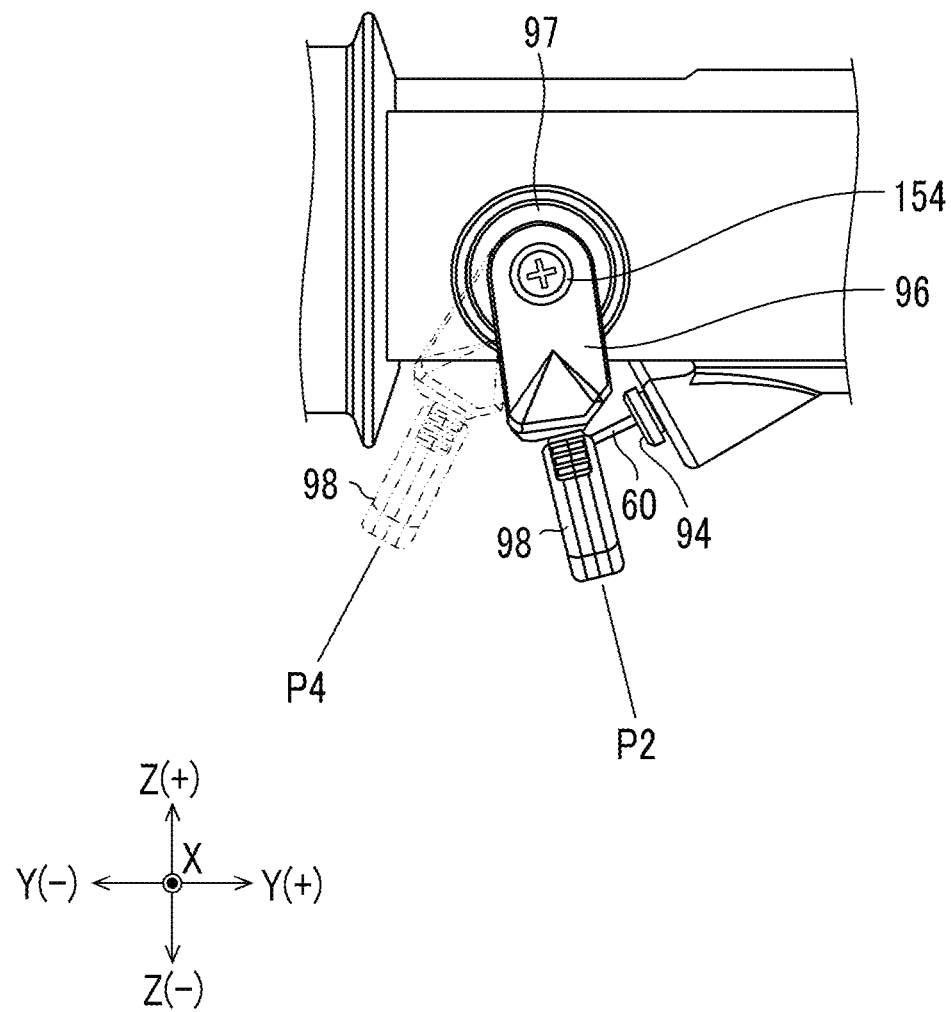
FIG. 24 is a diagram illustrating the operating range of a movable member.

FIG. 23 is a diagram illustrating the operating range of the elevating operation lever 20, and FIG. 24 is a diagram illustrating the operating range of the movable member 96. In a case where the elevating operation lever 20 is positioned at a proximal end position P1 of an operating region shown in FIG. 23 by a solid line, the movable member 96 is positioned at a distal end position P2 of an operating region shown in FIG. 24 by a solid line by the above-mentioned elevating operation mechanism 120. Accordingly, the wire 60 connected to the movable member 96 through the mounting member 98 is pushed to the distal end side, so that the elevator 30 is positioned at the fallen position shown in FIG. 4. In contrast, in a case where the elevating operation lever 20 is positioned at a distal end position P3 of an operating region shown in FIG. 23 by a two-dot chain line, the movable member 96 is positioned at a proximal end position P4 of an operating region shown in FIG. 24 by a two-dot chain line by the above-mentioned elevating operation mechanism 120. Accordingly, the wire 60 is pulled to the proximal end side, so that the elevator 30 is positioned at the elevated position shown in FIG. 3.

The elevating operation lever 20 comes into contact with the operation unit body 32, so that the operating range of the elevating operation lever 20 is regulated between the proximal end position P1 and the distal end position P3 having been already described. Accordingly, the operating range of the movable member 96 is also regulated between the distal end position P2 and the proximal end position P4 having been already described. The positional relationship between the elevating operation lever 20 and the movable member 96 has been described above.

In a case where the elevating operation lever 20 is positioned at the proximal end position P1 as described above, the elevator 30 can be positioned at the fallen position shown in FIG. 4. However, the elevator 30 cannot be positioned at the attachment/detachment position shown in FIGS. 5 and 12 in the rotating operation of the elevating operation lever 20.

Figure 25:
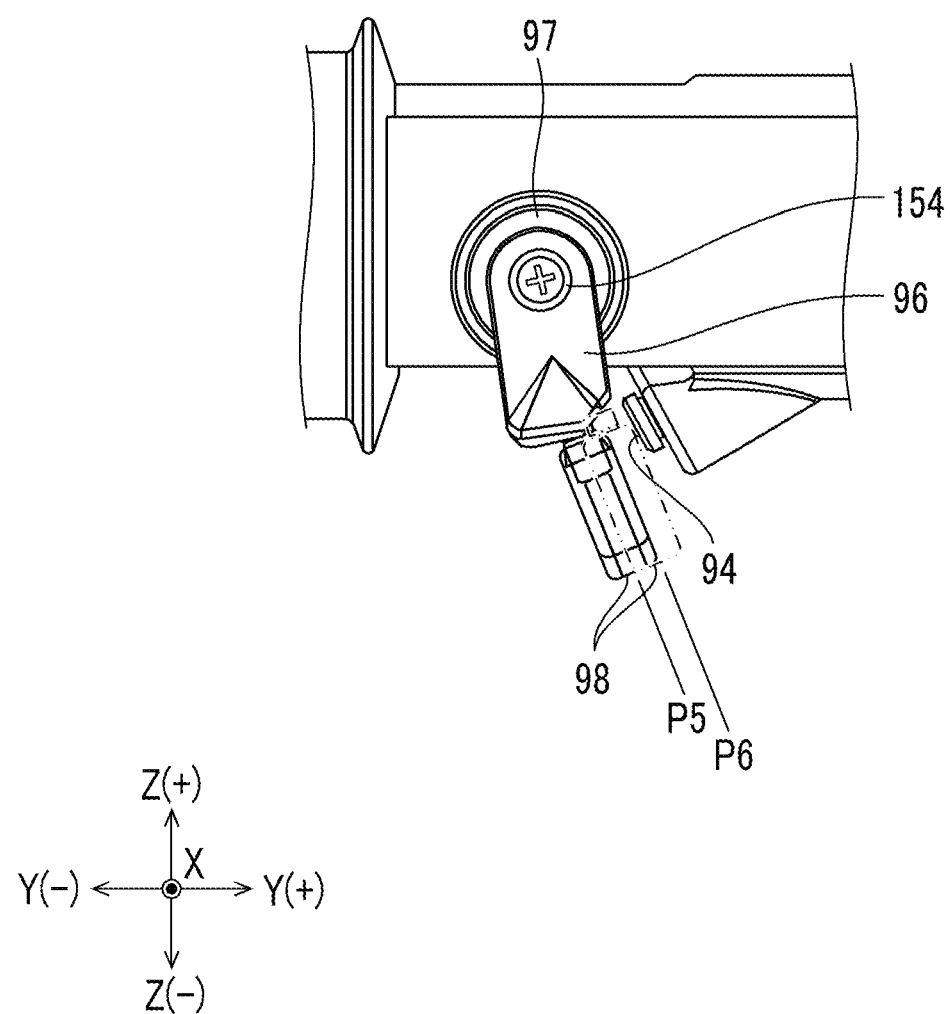
FIG. 25 is a diagram illustrating that a mounting member is positioned at a mounting position and a disengagement position.

For this reason, the following operation should be performed to position the elevator 30 at the attachment/detachment position. First, the mounting member 98 is detached from the movable member 96. Then, the mounting member 98 is pushed to a mounting position that is positioned closer to the distal end side from the distal end position P2. The mounting member 98 positioned at the mounting position P5 is shown in FIG. 25 by a solid line. Since the wire 60 can be further pushed to the distal end side by this operation, the elevator 30 can be positioned at the attachment/detachment position shown in FIGS. 5 and 12 and the engaging portion 100 can be engaged with the housing portion 102 at the attachment/detachment position.

On the other hand, in a case where the engaging portion 100 is to be disengaged from the housing portion 102, the mounting member 98 is pushed to a disengagement position P6 that is positioned closer to the distal end side from the mounting position P5 shown in FIG. 25 by a solid line and is shown in FIG. 25 by a two-dot chain line. Accordingly, since the wire 60 can be further pushed to the distal end side, the engaging portion 100 can be disengaged from the housing portion 102 by the above-mentioned inclined surface 114 for disengagement.

Next, the movable member 96 will be described.

Figure 30:
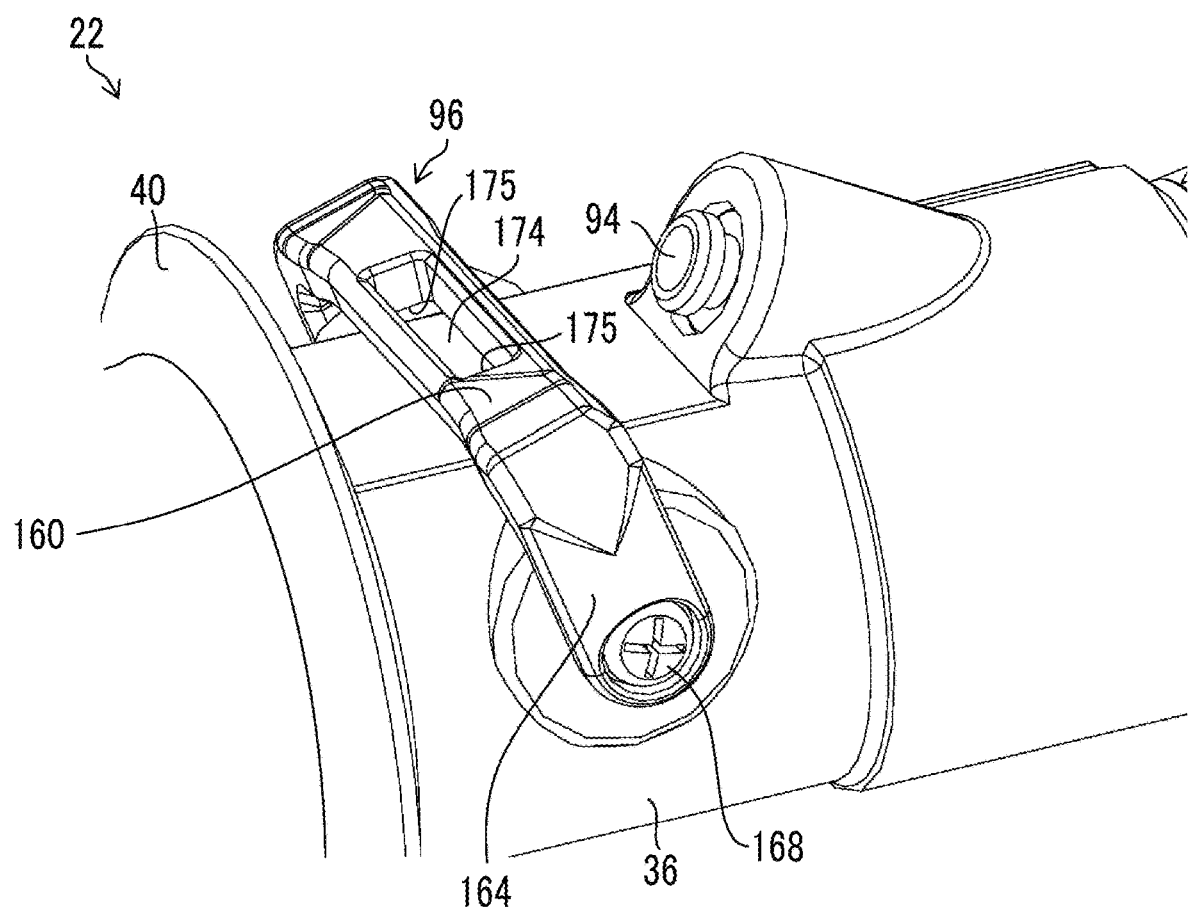
FIG. 30 is a perspective view of an extending part that includes an inlet and the movable member.
Figure 31:
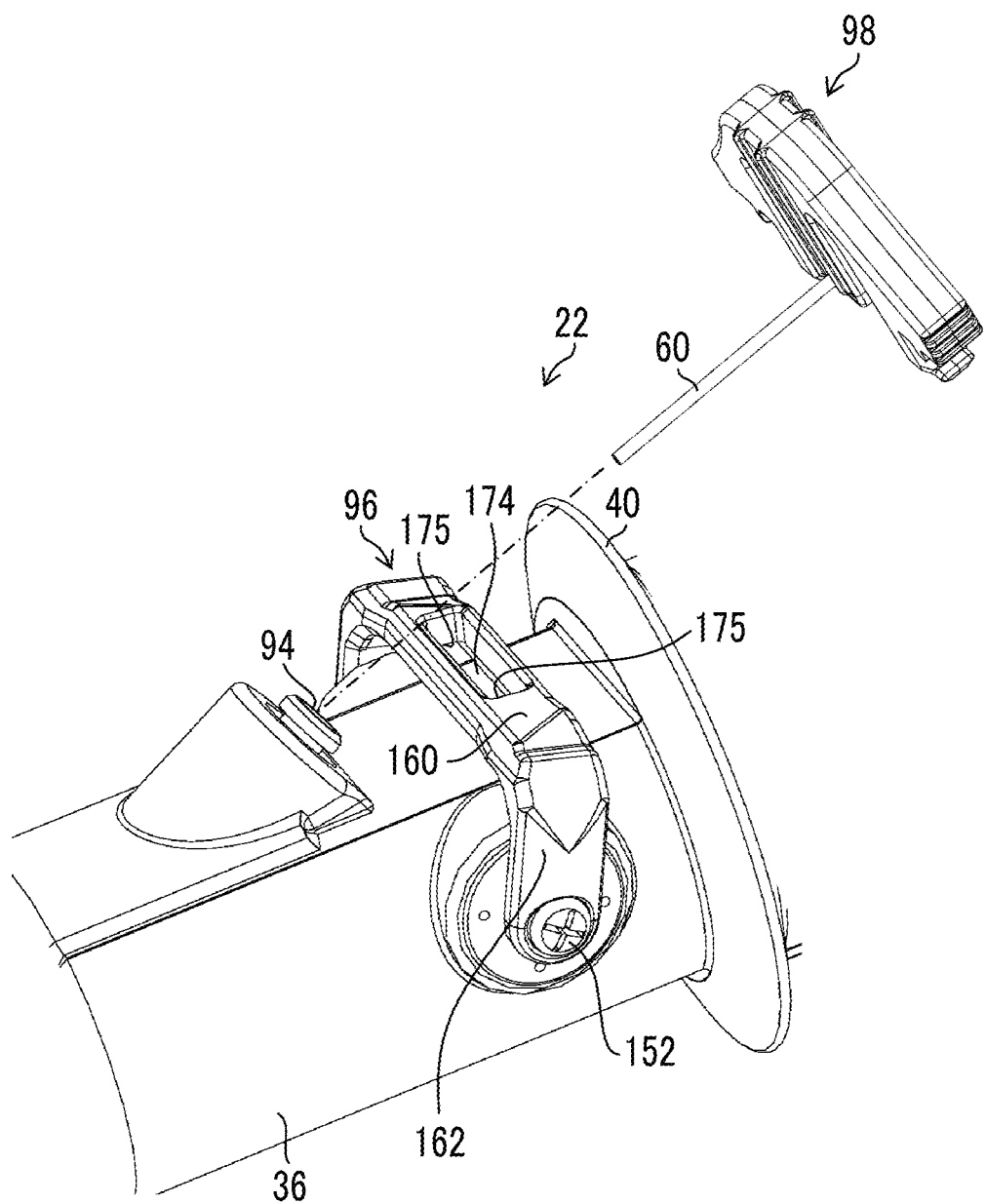
FIG. 31 is a diagram illustrating that a wire is introduced through the inlet so that the engaging portion becomes a leading end.

As shown in FIGS. 30 and 31 to be described later, the movable member 96 comprises a flat plate-shaped beam portion 160 and leg portions 162 and 164 provided at both ends of the beam portion 160 and is formed in a U-shape as a whole. Further, as shown in FIGS. 21 and 22, the drive shaft part 152 provided at the leg portion 162 is rotationally and movably supported on an exterior case (not shown) of the operation unit 22 through an O-ring 166, and a driven shaft part 168 provided at the leg portion 164 is rotationally and movably supported on the exterior case (not shown) through an O-ring (not shown). The watertightness of the operation unit 22 is kept by these O-rings 166.

Further, the rotation axes of the drive shaft part 152 and the driven shaft part 168 of the movable member 96 are set to a direction (X(+)-X(−) direction) perpendicular to the axial direction of the wire 60. That is, since the movable member 96 is provided to be rotatable about a direction, which is perpendicular to the axial direction of the wire 60, as a rotation axis, the movable member 96 can smoothly push or pull the wire 60.

Next, a mounting structure 170 of the embodiment for mounting the proximal end of the wire 60 on the movable member 96 will be described with reference to FIGS. 26 to 30.

Figure 26:
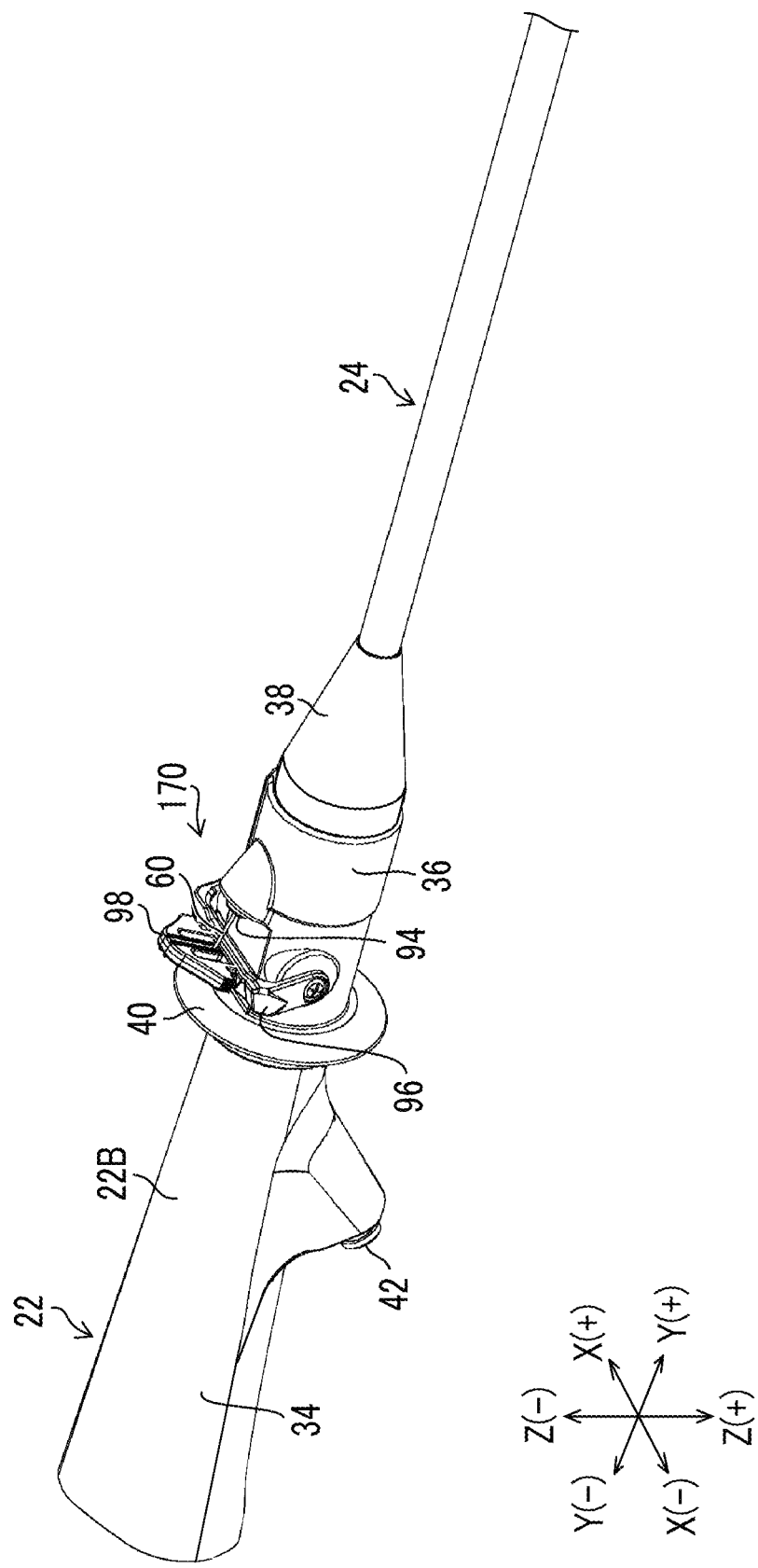
FIG. 26 is a perspective view of a mounting structure that is viewed from the other side surface of the operation unit.
Figure 27:
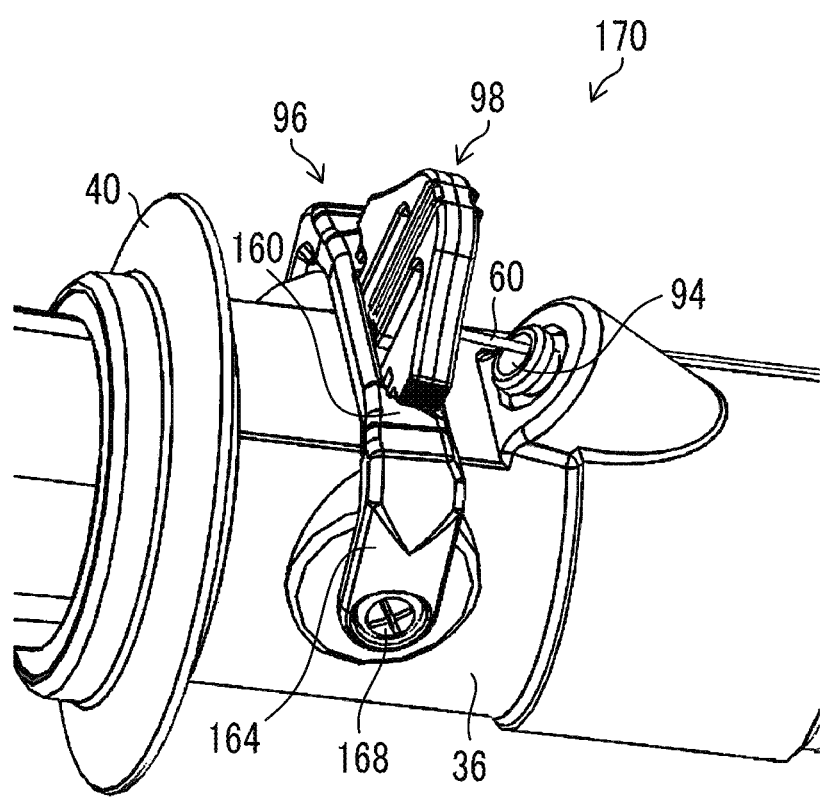
FIG. 27 is a perspective view of the mounting structure shown in FIG. 26 that is viewed from the left side.
Figure 28:
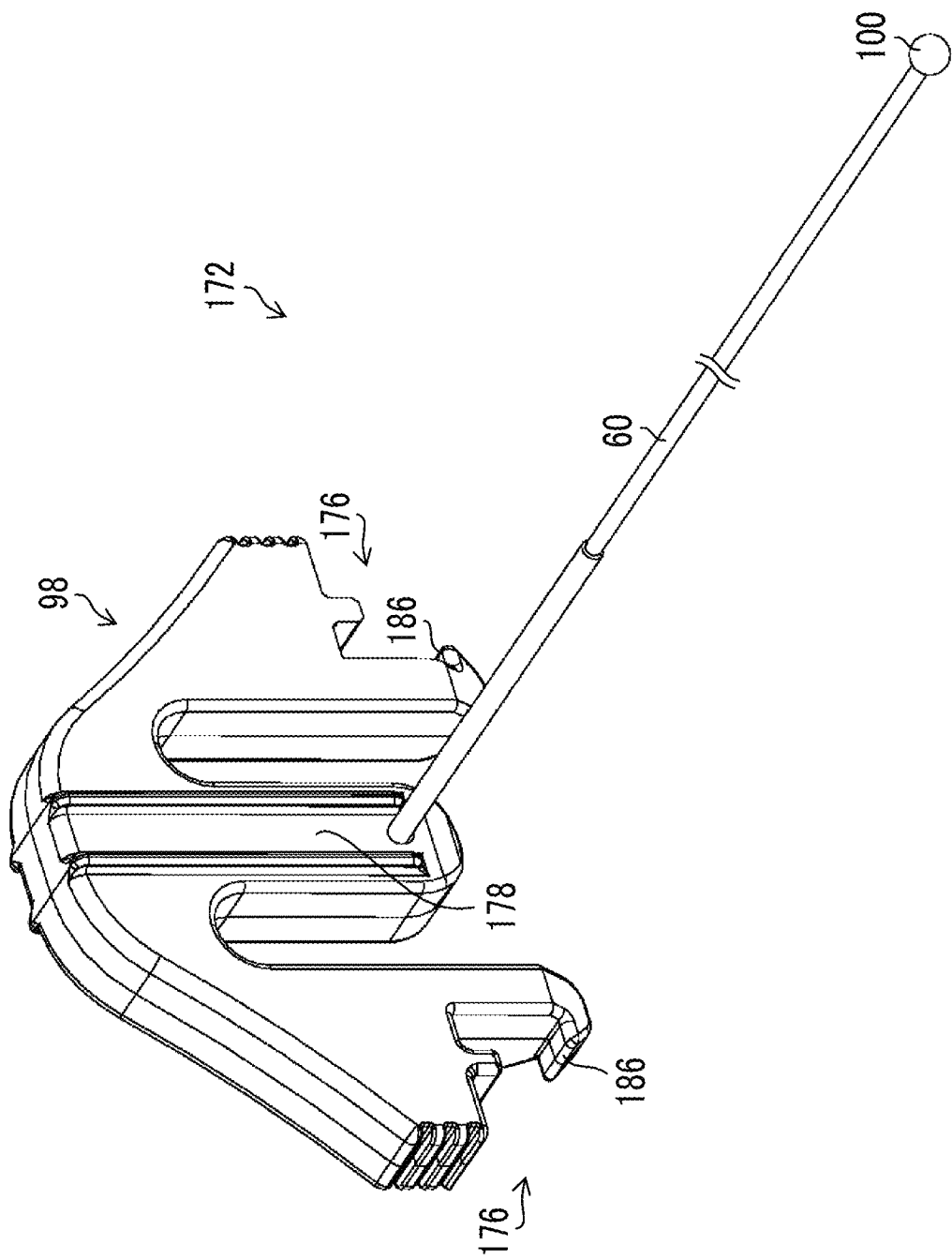
FIG. 28 is a perspective view of a wire assembly.
Figure 29:
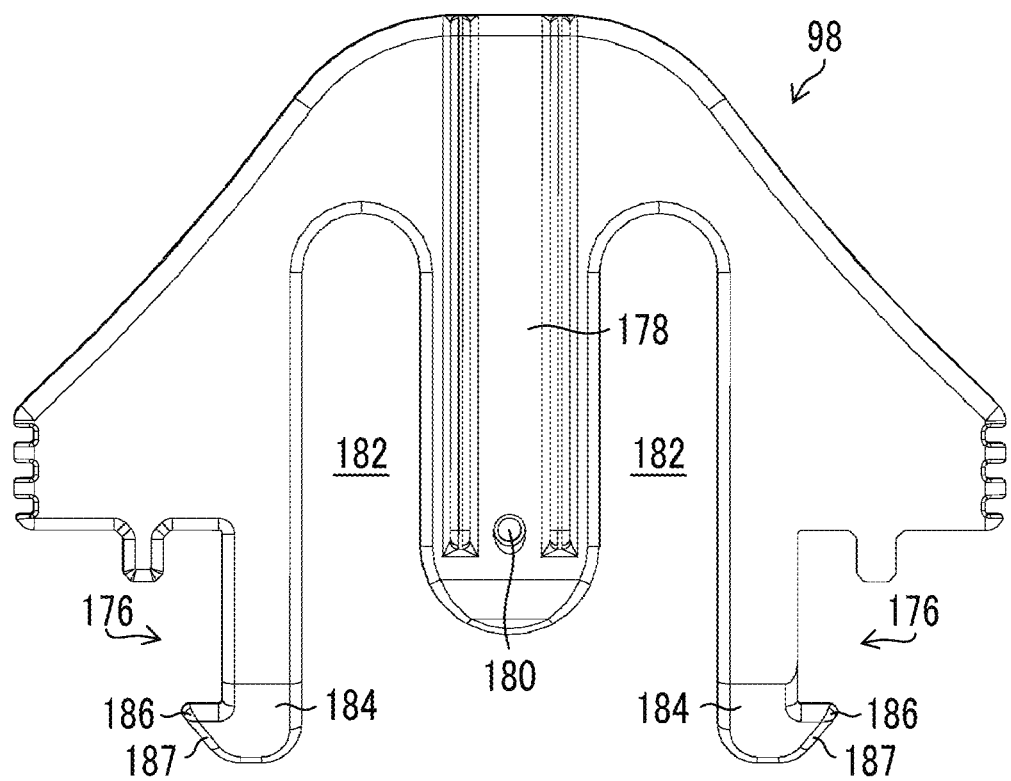
FIG. 29 is a front view of the mounting member 98.

FIG. 26 is a perspective view of the mounting structure 170 that is viewed from the other side surface 22B of the operation unit 22. Further, FIG. 27 is a perspective view of the mounting structure 170 shown in FIG. 26 that is viewed from the left side. Furthermore, FIG. 28 is a perspective view of a wire assembly 172 that comprises the wire 60 and the mounting member 98 provided at the proximal end of the wire 60. FIG. 29 is a front view of the mounting member 98, and FIG. 30 is a perspective view of the extending part 36 that includes the inlet 94 and the movable member 96.

As shown in FIG. 30, the movable member 96 is provided with an engaging hole 174 with which the mounting member 98 (see FIG. 29) is to be attachably and detachably engaged. The engaging hole 174 is formed of a through hole that is formed so as to extend in the longitudinal direction of the beam portion 160 of the movable member 96 and penetrates the surface and back of the beam portion 160. A pair of locking portions 176 and 176 (see FIG. 29) of the mounting member 98 is attachably and detachably engaged with the engaging hole 174.

The mounting member 98 shown in FIG. 29 is a substantially triangular plate-like body, and a hole portion 180 to which the proximal end of the wire 60 is to be connected is formed at a core portion 178 formed at the central portion of the mounting member 98. The pair of locking portions 176 and 176 of the mounting member 98 is provided on both sides of the core portion 178 with slit-like notches 182 interposed between the core portion 178 and themselves. Further, an elastically deformable portion 184, which is elastically deformed to be engaged with the engaging hole 174, is formed at each of the pair of locking portions 176 and 176. Furthermore, claw portions 186, which are to be locked to both edge portions 175 and 175 (see FIG. 30) of the engaging hole 174 in the longitudinal direction, are formed at the elastically deformable portions 184 and 184, respectively. In a case where the engaging hole 174 and the locking portions 176 and 176 are engaged with each other or disengaged from each other, these claw portions 186 and 186 are displaced so as to approach each other through the elastic deformation of the elastically deformable portions 184 and 184.

Next, a mounting procedure for mounting the proximal end portion of the wire 60 on the movable member 96 by the mounting structure 170 of the embodiment will be described.

First, work for engaging the distal end portion of the wire 60 with the elevator 30 is performed before the proximal end portion of the wire 60 is mounted on the movable member 96.

FIG. 31 is a diagram illustrating that the wire 60 is introduced through the inlet 94 so that the engaging portion 100 (see FIG. 28) becomes a leading end. Further, the cap member 76 shown in FIG. 2 is mounted on the distal end member 28 prior to the introduction of the wire 60.

In a case where the wire 60 is introduced through the inlet 94 as shown in FIG. 31 so that the engaging portion 100 becomes a leading end, the engaging portion 100 is led out of the outlet 74 shown in FIG. 6 through the wire channel 62 shown in FIG. 2 to the outside. Then, due to a successive operation for introducing the wire 60, the engaging portion 100 is guided toward the contact portion 101 of the elevator 30 by the wire guide portion 110 shown in FIG. 6 and comes into contact with the contact portion 101 as shown in FIG. 10. FIG. 10 shows a state where the engaging portion 100 is in contact with the contact portion 101 of the elevator 30 positioned at the elevated position. However, the position of the elevator 30 is not limited to the elevated position, and the engaging portion 100 is in contact with the contact portion 101 of the elevator 30 even though the elevator 30 is present at any position between the elevated position and the attachment/detachment position.

After that, in a case where the wire 60 is operated to be further introduced, a state where the engaging portion 100 is in contact with the contact portion 101 is maintained since the gap a between the contact portion 101 and the wall portion 81 facing the contact portion 101 is set to be equal to the diameter D of the engaging portion 100 and the gap b between the guide portion 106 for engagement and the wall portion 81 facing the guide portion 106 for engagement is set to be smaller than the diameter D of the engaging portion 100 as shown in FIG. 13. Accordingly, the elevator 30 is rotated in the fallen direction. Then, in a case where the elevator 30 reaches the fallen position shown in FIG. 11 from the elevated position and goes beyond the fallen position due to a successive operation of introducing the wire 60, the wall portion 81 is not present at a position facing the guide portion 106 for engagement. For this reason, the engaging portion 100 is moved toward the guide portion 106 for engagement from the contact portion 101 as shown in FIG. 14 and is guided toward the opening 104 of the housing portion 102 along the guide passage 108 as shown in FIG. 15. In this case, the elevator 30 is moved toward the attachment/detachment position shown in FIG. 12 in conjunction with an operation for pushing the wire 60. Then, in a case where the position of the elevator 30 is regulated to the attachment/detachment position by the position regulating member 77 (see FIG. 5), the engaging portion 100 is engaged with the housing portion 102 through the opening 104 due to the elastic restoring force of the wire 60 as shown in FIG. 16. Accordingly, the distal end portion of the wire 60 can be engaged with the elevator 30.

Therefore, according to the endoscope 10 of the embodiment, even though the elevator 30 is present at any position between the elevated position and the fallen position, the distal end portion of the wire 60 can be connected to the elevator 30 by only an operation for introducing the wire 60.

Figure 33:
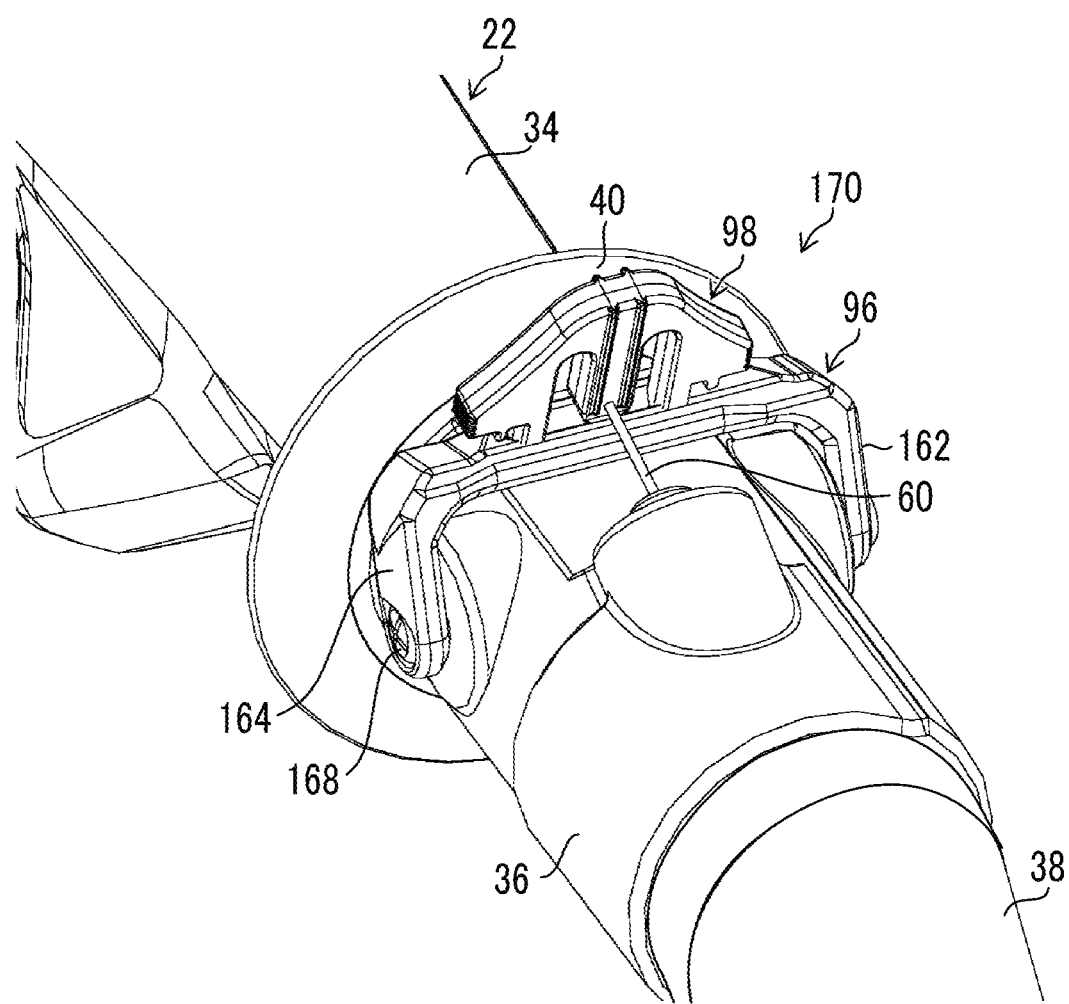
FIG. 33 is a perspective view showing that the mounting member is connected to the movable member.

FIG. 32 shows the attitude of the mounting member 98 in a state where the distal end portion of the wire 60 is connected to the elevator 30. In this case, the mounting member 98 is positioned at the mounting position P5 shown in FIG. 25. The mounting member 98 is moved toward the movable member 96 from the mounting position P5 as shown by an arrow g, so that tapered portions 187 and 187 formed at the lower portions of the claw portions 186 and 186 shown in FIG. 29 are in contact with both the edge portions 175 and 175 of the engaging hole 174 shown in FIG. 31 and the mounting member 98 is pushed into the engaging hole 174. An interval between the claw portions 186 and 186 is reduced by this operation for pushing the mounting member 98, so that the claw portions 186 and 186 are locked to both the edge portions 175 and 175 of the engaging hole 174. Accordingly, the mounting member 98 is connected to the movable member 96 as shown in a connection diagram of FIG. 33. Therefore, according to the mounting structure 170 of the embodiment, the proximal end of the wire 60 can be mounted on the movable member 96 with one touch by only work for pushing the claw portions 186 and 186 of the mounting member 98 into the engaging hole 174 of the movable member 96.

After that, in a case where the elevating operation lever 20 shown in FIG. 23 is operated, the movable member 96 operates between the distal end position P2 and the proximal end position P4 as shown in FIG. 24. Then, the wire 60 is operated to be pushed or pulled by the movable member 96 through the mounting member 98 in conjunction with the operation of the movable member 96. Accordingly, the elevator 30 is moved rotationally between the elevated position and the fallen position.

In a case where the elevator 30 is moved rotationally between the elevated position and the fallen position, a state where the engaging portion 100 is engaged with the housing portion 102 is kept between the elevated position shown in FIG. 3 and the fallen position shown in FIG. 4 by the retaining portion 112 of the partition wall 80 shown in FIG. 17. Accordingly, the inadvertent separation of the engaging portion 100 from the housing portion 102 is prevented. Therefore, according to the endoscope 10 of the embodiment, the elevator 30 can be reliably operated by the operation of the elevating operation lever 20.

Incidentally, the endoscope 10 is used for various examinations or treatments. Then, the following work is performed in a case where the endoscope 10 is to be washed.

First, a user pinches the locking portions 176 and 176 of the mounting member 98 with fingers, reduces an interval between the claw portions 186 and 186 so that the interval is smaller than the length of the engaging hole 174 in the longitudinal direction, and then pulls the claw portions 186 and 186 out of the engaging hole 174.

After that, the user pushes the mounting member 98 toward the disengagement position P6 shown in FIG. 25 by a two-dot chain line. Accordingly, since the wire 60 is pushed to the distal end side, the engaging portion 100 is disengaged from the housing portion 102 by the above-mentioned inclined surface 114 for disengagement. Therefore, according to the endoscope 10 of the embodiment, the distal end portion of the wire 60 can be easily detached from the elevator 30.

Next, after pulling the wire 60 out of the inlet 94 to empty the wire channel 62, the user detaches the cap member 76 shown in FIG. 2 from the distal end member 28. Meanwhile, after detaching the cap member 76 from the distal end member 28, the user may pull the wire 60 out of the inlet 94 to empty the wire channel 62. After that, the distal end member 28, the elevator 30, and the wire channel 62 are washed.

As described above, according to the endoscope 10 of the embodiment, the elevator 30 starts to be rotated toward the fallen position in a case where the wire 60 is introduced and the engaging portion 100 comes into contact with the contact portion 101. Then, in a case where the elevator 30 is being rotated toward the fallen position, the wall portion 81 regulates the movement of the engaging portion 100 in a direction where the engaging portion 100 enters the opening 104. After that, in a case where the elevator 30 is being rotated toward the attachment/detachment position from the fallen position, the wall portion 81 allows the movement of the engaging portion 100 in a direction where the engaging portion 100 enters the opening 104. Then, in a case where the elevator 30 reaches the attachment/detachment position, the engaging portion 100 is housed in the housing portion 102.

According to the endoscope 10 of the embodiment, since the contact portion 101 and the wall portion 81 are provided, the distal end portion of the wire 60 can be connected to the elevator 30 by only an operation for introducing the wire 60 even though the elevator 30 is present at any position between the elevated position and the fallen position. Therefore, according to the endoscope 10 of the embodiment, the distal end portion of the wire 60 and the elevator 30 can be easily connected to each other.

The partition wall 80 has been provided with the wall portion 81 and the retaining portion 112 in the embodiment, but the cap member 76 may be provided with the wall portion 81 and the retaining portion 112. Further, the partition wall 80 may be provided with one of the wall portion 81 and the retaining portion 112, and the cap member 76 may be provided with the other of the wall portion 81 and the retaining portion 112.

Furthermore, the cap member 76 has been provided with the position regulating member 77 (see FIG. 5) in the embodiment, but the distal end member 28 may be provided with the position regulating member 77. Moreover, since the engaging portion 100 is housed in the housing portion 102 in a case where the elevator 30 is positioned at the attachment/detachment position, the position regulating member 77 is not a necessarily necessary member.

Further, the engaging hole 174 has been formed at the movable member 96 and the locking portions 176 have been formed at the mounting member 98 in the mounting structure 170 of the embodiment, but the locking portions 176 may be formed at the movable member 96 and the engaging hole 174 may be formed at the mounting member 98. That is, any one of the movable member 96 or the mounting member 98 may be provided with the engaging hole 174 and the other thereof may be provided with the locking portions 176 that are attachably and detachably engaged with the engaging hole 174. Furthermore, the claw portions 186 may be provided on the beam portion 160 of the movable member 96 not in the longitudinal direction but in a lateral direction. Moreover, the engaging hole 174 may be two engaging holes that are formed so as to be separated from each other in the longitudinal direction of the beam portion 160. Further, the engaging hole 174 may be a recessed non-through hole that does not penetrate the surface and back of the beam portion 160.

Furthermore, the wire 60 has been pulled out of the inlet 94 to empty the wire channel 62 in the above-mentioned example, but the invention is not limited thereto. For example, in a case where the proximal end of the wire 60 is detached from the mounting member 98 prior to the pull of the wire 60 out of the wire channel 62, the wire 60 can be pulled out of the outlet 74.

Further, the notch surfaces 84A and 86A have been formed on the rotational movement shaft portions 84 and 86 of the elevator 30 as shown in FIG. 7 in the above-mentioned example to improve the washability of the bearing portions 78A and 80A, but the same effect can be obtained even from the following aspects.

Figure 34:
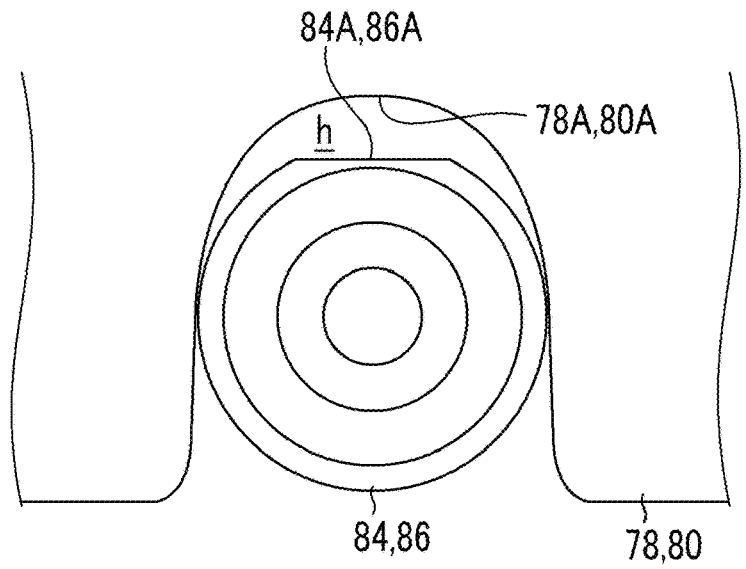
FIG. 34 is a diagram illustrating that the shape of the inner peripheral surface of a bearing portion of the elevator is a chevron shape.

That is, in a case where the shapes of the inner peripheral surface of the bearing portions 78A and 80A are set to a chevron shape to form large gaps h between the inner peripheral surface of the bearing portions 78A and 80A and the rotational movement shaft portions 84 and 86 as shown in FIG. 34, a brush can be easily inserted into the gaps h. Accordingly, the washability of the bearing portions 78A and 80A can be improved.

Figure 35:
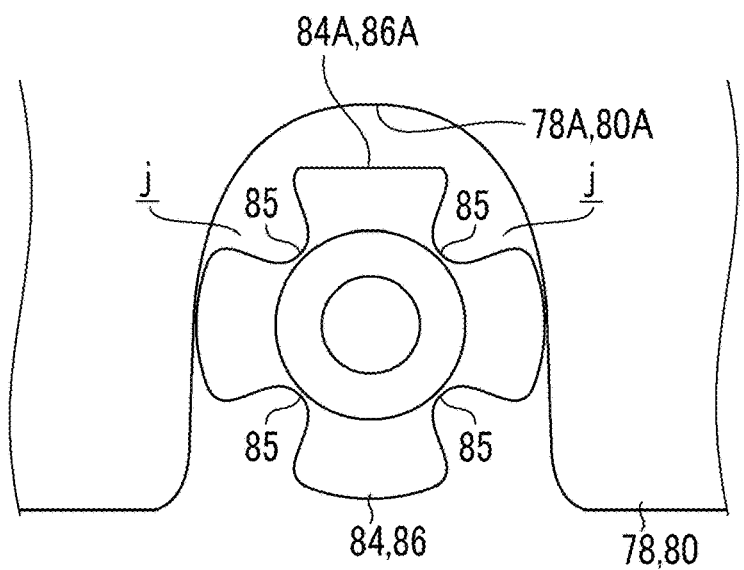
FIG. 35 is a diagram illustrating that a plurality of grooves are formed on the outer peripheral surfaces of rotational movement shaft portions of the elevator.

Further, in a case where a plurality of grooves 85 are formed on the outer peripheral surfaces of the rotational movement shaft portions 84 and 86 as shown in FIG. 35, a brush is easily inserted into gaps j between the grooves 85 and the bearing portions 78A and 80A. Accordingly, the washability of the bearing portions 78A and 80A can be improved.

The endoscope 10 where the proximal end side of the wire 60 is connected to the elevating operation lever 20 through the mounting member 98, the movable member 96, and the elevating operation mechanism 120 has been exemplified in the embodiment, but the invention is not limited thereto. For example, the invention can also be applied to an endoscope where the proximal end of the wire 60 is directly connected to the elevating operation mechanism 120 to connect the proximal end side of the wire 60 is connected to the elevating operation lever 20.

Further, a duodenoscope has been exemplified as the endoscope 10 in the embodiment. However, as long as an endoscope comprises an elevator that is provided at a distal end part of an insertion unit and adjusts the lead-out direction of a treatment tool, the invention can be applied to various endoscopes, such as an ultrasound endoscope.

EXPLANATION OF REFERENCES

10: endoscope
12: endoscope system
14: processor device
16: light source device
18: display
20: elevating operation lever
22: operation unit
22A: one side surface
22B: the other side surface
24: insertion unit
26: distal end part
28: distal end member
28A: peripheral surface
30: elevator
30A: guide surface
30B: base portion
32: operation unit body
34: grip part
36: extending part
38: bending-proof pipe
38A: proximal end portion
40: flange
42: treatment tool inlet
44: mount portion
44A: distal end portion
46: universal cord
48: electrical connector
50: light source connector
52: bendable part
54: soft part
56: treatment tool
56A: distal end portion
58: treatment tool channel
60: wire
62: wire channel
64: angle knob
66: air/water supply button
68: suction button
70: air/water supply nozzle
72: treatment tool outlet
74: outlet
76: cap member
76A: open window 77: position regulating member
78: partition wall
78A: bearing portion
80: partition wall
81: wall portion
80A: bearing portion
82: elevator-housing chamber
84: rotational movement shaft portion
85: groove
84A: notch surface
86: rotational movement shaft portion
86A: notch surface
88: optical system-housing chamber
90: illumination window
92: observation window
94: inlet
95: valve element
96: movable member
98: mounting member
98A: mounting member
100: engaging portion
101: contact portion
102: housing portion
104: opening
106: guide portion for engagement
108: guide passage
110: wire guide portion
112: retaining portion
114: inclined surface for disengagement
120: elevating operation mechanism
124: first conversion mechanism
126: wire
128: second conversion mechanism
130: crank member
132: first slider
134: second slider
136: lever
138: first gear
140: second gear
142: third gear
144: fourth gear
146: bracket
148: shaft part
150: shaft part
152: drive shaft part
160: beam portion
160A: back
162: leg portion
164: leg portion
166: O-ring
168: driven shaft part
170: mounting structure
172: wire assembly
174: engaging hole
174A: engaging hole
175: edge portion
176: locking portion
178: core portion
180: hole portion
182: notch
184: elastically deformable portion
186: claw portion
187: tapered portion
200: branch pipe
202: distal end pipe
204: pipe line
206: pipe line
208: suction pipe

What is claimed is:

1. An endoscope comprising:
a hand operation unit that comprises an operation member;
an insertion unit of which a proximal end portion is connected to the hand operation unit;
a distal end member that is provided at a distal end part of the insertion unit;
a treatment tool-elevator that is mounted on the distal end member so as to be rotationally movable and is rotationally movable in a rotational movement range from an elevated position up to an attachment/detachment position beyond a fallen position;
an elevating operation wire of which a distal end side is connected to the treatment tool-elevator and a proximal end side is connected to the operation member and which is pushed or pulled according to an operation of the operation member to cause the treatment tool-elevator to be rotationally moved in the rotational movement range between the elevated position and the fallen position;
an engaging portion that is provided at a distal end portion of the elevating operation wire;
an inlet which is provided on the hand operation unit and through which the elevating operation wire is introduced so that the engaging portion becomes a leading end;
an outlet which is provided at the distal end member and out of which the elevating operation wire is led so that the engaging portion becomes the leading end;
a wire insertion channel that is provided in the insertion unit and allows the inlet and the outlet to communicate with each other;
a contact portion that is provided on the treatment tool-elevator and applies a rotational moving force acting in a fallen direction to the treatment tool-elevator in a case where the engaging portion led out of the outlet is in contact with the contact portion;
a housing portion which is provided on the treatment tool-elevator and in which an opening for housing the engaging portion is formed; and
a wall portion that is provided at a position adjacent to the treatment tool-elevator and facing a movement trajectory of the engaging portion in a case where the treatment tool-elevator is moved between the elevated position and the fallen position in a state where the engaging portion is in contact with the contact portion,
wherein in a state where the engaging portion is in contact with the contact portion, the wall portion regulates movement of the engaging portion in a direction where the engaging portion enters the opening in a case where the treatment tool-elevator is present between the elevated position and the fallen position and allows movement of the engaging portion in the direction where the engaging portion enters the opening in a case where the treatment tool-elevator is present between the fallen position and the attachment/detachment position.

2. The endoscope according to claim 1,
wherein the distal end member is provided with a wire guide portion that guides the engaging portion led out of the outlet to the contact portion.

3. The endoscope according to claim 1,
wherein the treatment tool-elevator is provided with a guide portion for engagement that guides the engaging portion to the opening.

4. The endoscope according to claim 3,
wherein the guide portion for engagement includes a guide passage that guides the engaging portion in a direction where the engaging portion is separated from the opening.

5. The endoscope according to claim 1, further comprising:
a retaining portion that is provided at a position adjacent to the treatment tool-elevator and facing the movement trajectory of the engaging portion in a case where the treatment tool-elevator is moved between the elevated position and the fallen position in a state where the engaging portion is housed in the housing portion, and maintains a state where the housing portion and the engaging portion are engaged with each other.

6. The endoscope according to claim 5,
wherein a cap member is attachably and detachably mounted on the distal end member, and
any one of the distal end member or the cap member comprises the wall portion or the retaining portion.

7. The endoscope according to claim 6,
wherein the cap member comprises a position regulating member, and
in a case where the cap member is mounted on the distal end member, the position regulating member is in contact with the treatment tool-elevator and regulates a position where the treatment tool-elevator is most fallen to the attachment/detachment position.

8. The endoscope according to claim 1,
wherein an inclined surface for disengagement, which is widened toward an outside of the opening, is formed on an inner surface, which corresponds to a lead-out direction of the engaging portion, in the inner surface of the housing portion close to the opening.

9. The endoscope according to claim 1, further comprising:
a movable member that is disposed to be exposed to an outside of the hand operation unit and operates in conjunction with an operation of the operation member; and
a mounting member that is provided at a proximal end of the elevating operation wire and is attachably and detachably engaged with the movable member.

10. The endoscope according to claim 9,
wherein any one of the movable member or the mounting member is provided with an engaging hole and the other thereof is provided with a locking portion to be attachably and detachably engaged with the engaging hole.

11. The endoscope according to claim 10,
wherein the locking portion is provided with an elastically deformable portion that is elastically deformed to be engaged with the engaging hole.

12. The endoscope according to claim 11,
wherein a pair of elastically deformable claw portions to be locked to edge portions of the engaging hole is formed at the elastically deformable portion, and the pair of claw portions is displaced so as to approach each other through elastic deformation in a case where the engaging hole and the locking portion are engaged with each other or disengaged from each other.

* * * * *